(12) United States Patent
Singh et al.

(10) Patent No.: US 12,144,529 B2
(45) Date of Patent: Nov. 19, 2024

(54) BONE PLATES AND ASSOCIATED SCREWS

(71) Applicant: Stryker European Operations Limited, Carrigtwohill (IE)

(72) Inventors: Manoj Kumar Singh, Mahwah, NJ (US); Subash K. Mannanal, Mahwah, NJ (US); Robert Dominik, Grandvaux (CH); Pierre-Luc Sylvestre, Grenchen (CH); Andreas Wiederkehr, Biel/Bienne (CH)

(73) Assignee: Stryker European Operations Limited, Carrigtwohill (IE)

( * ) Notice: Subject to any disclaimer, the term of this patent is extended or adjusted under 35 U.S.C. 154(b) by 619 days.

(21) Appl. No.: 17/332,090

(22) Filed: May 27, 2021

(65) Prior Publication Data

US 2021/0282824 A1    Sep. 16, 2021

Related U.S. Application Data

(63) Continuation of application No. 16/289,826, filed on Mar. 1, 2019, now Pat. No. 11,039,865.

(60) Provisional application No. 62/637,695, filed on Mar. 2, 2018.

(51) Int. Cl.
*A61B 17/80* (2006.01)
*A61B 17/86* (2006.01)

(52) U.S. Cl.
CPC ...... *A61B 17/8047* (2013.01); *A61B 17/8014* (2013.01); *A61B 17/8038* (2013.01); *A61B 17/8057* (2013.01); *A61B 17/8605* (2013.01)

(58) Field of Classification Search
CPC .............. A61B 17/8052; A61B 17/8047
See application file for complete search history.

(56) References Cited

U.S. PATENT DOCUMENTS

| | | | |
|---|---|---|---|
| 5,275,601 | A | 1/1994 | Gogolewski et al. |
| 5,405,394 | A | 4/1995 | Davidson |
| 5,904,683 | A | 5/1999 | Pohndorf et al. |
| 5,954,722 | A | 9/1999 | Bono |
| 6,030,389 | A | 2/2000 | Wagner et al. |

(Continued)

FOREIGN PATENT DOCUMENTS

| | | |
|---|---|---|
| AU | 2005314509 A1 | 6/2006 |
| AU | 2010201283 A1 | 4/2010 |

(Continued)

OTHER PUBLICATIONS

Extended European Search Report issued in Appln. No. 22189655.8 dated Nov. 10, 2022 (9 pages).

(Continued)

*Primary Examiner* — Andrew Yang
(74) *Attorney, Agent, or Firm* — Lerner David LLP

(57) ABSTRACT

A bone plate includes a bone-contacting surface, an upper surface opposite the bone-contacting surface, and a hole having a circumference and extending from the upper surface to the bone-contacting surface. The hole includes a first portion having a plurality of substantially parallel lips, each lip extends around the circumference of the hole and defines a diameter of the hole. The diameters of the hole, as defined by the lips, decrease in a direction from the upper surface to a center of the hole and increase in a direction from the center of the hole toward the bone-contacting surface.

19 Claims, 32 Drawing Sheets

(56) References Cited

U.S. PATENT DOCUMENTS

| | | |
|---|---|---|
| 6,206,881 B1 | 3/2001 | Frigg et al. |
| 6,322,522 B1 | 11/2001 | Zimmon |
| 6,322,562 B1 | 11/2001 | Wolter |
| 6,454,769 B2 | 9/2002 | Wagner et al. |
| 6,679,883 B2 | 1/2004 | Hawkes et al. |
| 6,767,351 B2 | 7/2004 | Orbay et al. |
| 6,902,565 B2 | 6/2005 | Berger et al. |
| 6,955,677 B2 | 10/2005 | Dahners |
| 6,974,461 B1 | 12/2005 | Wolter |
| 7,048,739 B2 | 5/2006 | Konieczynski et al. |
| 7,073,997 B2 | 7/2006 | Kovac |
| 7,137,987 B2 | 11/2006 | Patterson et al. |
| 7,175,624 B2 | 2/2007 | Konieczynski et al. |
| 7,179,260 B2 | 2/2007 | Gerlach et al. |
| 7,311,712 B2 | 12/2007 | Dalton |
| 7,318,825 B2 | 1/2008 | Butler et al. |
| 7,341,589 B2 | 3/2008 | Weaver et al. |
| 7,572,280 B2 | 8/2009 | Dickinson et al. |
| 7,635,364 B2 | 12/2009 | Barrall et al. |
| 7,637,928 B2 | 12/2009 | Fernandez |
| 7,682,379 B2 | 3/2010 | Mathieu et al. |
| 7,695,472 B2 | 4/2010 | Young |
| 7,695,502 B2 | 4/2010 | Orbay et al. |
| 7,766,947 B2 | 8/2010 | Hawkes et al. |
| 7,776,076 B2 | 8/2010 | Grady, Jr. et al. |
| 7,794,482 B2 | 9/2010 | Mathieu et al. |
| 7,837,717 B2 | 11/2010 | Deffenbaugh et al. |
| 7,842,037 B2 | 11/2010 | Schulze |
| 7,857,839 B2 | 12/2010 | Duong et al. |
| 7,883,531 B2 | 2/2011 | de Coninck |
| 7,905,909 B2 | 3/2011 | Orbay et al. |
| 7,905,910 B2 | 3/2011 | Gerlach et al. |
| 7,909,858 B2 | 3/2011 | Gerlach et al. |
| 7,931,678 B2 | 4/2011 | Konieczynski et al. |
| 7,931,681 B2 | 4/2011 | Carls et al. |
| 7,942,913 B2 | 5/2011 | Ziolo et al. |
| 7,951,178 B2 | 5/2011 | Jensen |
| 8,007,523 B2 | 8/2011 | Wagner et al. |
| 8,012,188 B2 | 9/2011 | Melkent et al. |
| 8,025,677 B2 | 9/2011 | Freid et al. |
| 8,066,750 B2 | 11/2011 | Oi et al. |
| 8,100,955 B2 | 1/2012 | Blain et al. |
| 8,105,367 B2 | 1/2012 | Austin et al. |
| 8,114,080 B2 | 2/2012 | Schulze |
| 8,118,846 B2 | 2/2012 | Either et al. |
| 8,128,628 B2 | 3/2012 | Freid et al. |
| 8,177,820 B2 | 5/2012 | Anapliotis et al. |
| 8,211,154 B2 | 7/2012 | Fisher et al. |
| 8,216,283 B2 | 7/2012 | Mathieu et al. |
| 8,216,312 B2 | 7/2012 | Gray |
| 8,226,692 B2 | 7/2012 | Mathieu et al. |
| 8,257,355 B2 | 9/2012 | Chin et al. |
| 8,262,659 B2 | 9/2012 | Ryan et al. |
| 8,282,675 B2 | 10/2012 | Maguire et al. |
| 8,287,575 B2 | 10/2012 | Murner et al. |
| 8,309,521 B2 | 11/2012 | Zhang et al. |
| 8,337,535 B2 | 12/2012 | White et al. |
| 8,343,196 B2 | 1/2013 | Schneider |
| 8,343,198 B2 | 1/2013 | Sommer et al. |
| 8,348,980 B2 | 1/2013 | Prasad et al. |
| 8,361,125 B2 | 1/2013 | Taylor et al. |
| 8,361,126 B2 | 1/2013 | Perrow et al. |
| 8,366,751 B2 | 2/2013 | Pfefferle et al. |
| 8,382,807 B2 | 2/2013 | Austin et al. |
| 8,388,666 B2 | 3/2013 | Castaneda et al. |
| 8,394,130 B2 | 3/2013 | Orbay et al. |
| 8,435,297 B2 | 5/2013 | Zubok et al. |
| 8,470,039 B2 | 6/2013 | Blain |
| 8,486,118 B2 | 7/2013 | Mathieu et al. |
| 8,496,692 B2 | 7/2013 | Bhatnagar et al. |
| 8,496,708 B2 | 7/2013 | Blain |
| 8,506,567 B2 | 8/2013 | Ziemek et al. |
| 8,506,607 B2 * | 8/2013 | Eckhof ............ A61B 17/8057 606/915 |
| 8,535,354 B2 | 9/2013 | Cummins |
| 8,551,107 B2 | 10/2013 | Ng et al. |
| 8,551,144 B2 | 10/2013 | Youssef et al. |
| 8,556,944 B2 | 10/2013 | Dube et al. |
| 8,574,268 B2 | 11/2013 | Chan et al. |
| 8,574,270 B2 | 11/2013 | Hess et al. |
| 8,632,574 B2 | 1/2014 | Kortenbach et al. |
| 8,641,740 B2 | 2/2014 | Kuster et al. |
| 8,672,982 B2 | 3/2014 | Rabiner et al. |
| 8,685,069 B2 | 4/2014 | Courtney et al. |
| 8,690,931 B2 | 4/2014 | Appenzeller et al. |
| 8,696,721 B2 | 4/2014 | Blain |
| 8,702,762 B2 | 4/2014 | Jacene et al. |
| 8,728,129 B2 | 5/2014 | Fritzinger et al. |
| 8,734,495 B2 | 5/2014 | Black |
| 8,747,441 B2 | 6/2014 | Konieczynski et al. |
| 8,777,999 B2 | 7/2014 | Songer |
| 8,808,333 B2 | 8/2014 | Kuster et al. |
| 8,814,869 B2 | 8/2014 | Freid et al. |
| 8,834,536 B2 | 9/2014 | Elsbury |
| 8,845,697 B2 | 9/2014 | Montello et al. |
| 8,845,698 B2 | 9/2014 | Schneider |
| 8,852,245 B2 | 10/2014 | Schneider |
| 8,864,802 B2 | 10/2014 | Schwager et al. |
| 8,870,931 B2 | 10/2014 | Dahners et al. |
| 8,876,873 B2 | 11/2014 | Schneider |
| 8,888,824 B2 | 11/2014 | Austin et al. |
| 8,900,277 B2 | 12/2014 | Perrow et al. |
| 8,906,076 B2 * | 12/2014 | Mocanu ............ A61B 17/8625 606/291 |
| 8,940,028 B2 | 1/2015 | Austin et al. |
| 8,992,581 B2 | 3/2015 | Austin et al. |
| 8,998,963 B2 | 4/2015 | Ziolo et al. |
| 9,072,548 B2 | 7/2015 | Matityahu |
| 9,101,423 B2 | 8/2015 | Hulliger |
| 9,103,367 B2 | 8/2015 | Arnett |
| 9,107,678 B2 | 8/2015 | Murner et al. |
| 9,125,699 B2 | 9/2015 | Zahrly et al. |
| 9,138,271 B2 | 9/2015 | Black |
| 9,149,311 B2 | 10/2015 | Elsbury |
| 9,149,367 B2 | 10/2015 | Davenport et al. |
| 9,168,075 B2 | 10/2015 | Dell'Oca |
| 9,186,189 B2 | 11/2015 | Campbell et al. |
| 9,192,419 B2 | 11/2015 | McDonough et al. |
| 9,220,547 B2 | 12/2015 | Blain et al. |
| 9,220,548 B2 | 12/2015 | Duong et al. |
| 9,259,255 B2 | 2/2016 | Lewis et al. |
| 9,265,546 B2 | 2/2016 | Blain |
| 9,271,771 B2 | 3/2016 | Mathieu et al. |
| 9,277,947 B2 | 3/2016 | Koay et al. |
| 9,295,505 B2 | 3/2016 | Schneider |
| 9,314,284 B2 | 4/2016 | Chan et al. |
| 9,320,552 B2 | 4/2016 | Jacene et al. |
| 9,351,774 B2 | 5/2016 | Konieczynski et al. |
| 9,358,051 B2 | 6/2016 | Sournac et al. |
| 9,364,342 B2 | 6/2016 | Walkenhorst et al. |
| 9,387,022 B2 | 7/2016 | Koay et al. |
| 9,404,525 B2 | 8/2016 | Arnett |
| 9,408,646 B2 | 8/2016 | Rathbun et al. |
| 9,414,870 B2 | 8/2016 | Ryan et al. |
| 9,414,935 B2 | 8/2016 | McDonough et al. |
| 9,421,005 B2 | 8/2016 | Bonutti et al. |
| 9,433,443 B2 | 9/2016 | Montello et al. |
| 9,468,482 B2 | 10/2016 | Black |
| 9,474,558 B2 | 10/2016 | Sixto, Jr. et al. |
| 9,510,880 B2 | 12/2016 | Terrill et al. |
| 9,545,275 B2 | 1/2017 | Cawley et al. |
| 9,545,278 B2 | 1/2017 | Ducharme et al. |
| 9,554,837 B2 | 1/2017 | Schonhardt et al. |
| 9,585,707 B2 | 3/2017 | Blain |
| 9,603,641 B2 | 3/2017 | Hulliger |
| 9,603,716 B2 | 3/2017 | Zubok et al. |
| 9,629,725 B2 | 3/2017 | Lubensky et al. |
| 9,615,866 B1 | 4/2017 | Smith et al. |
| 9,655,665 B2 | 5/2017 | Perrow |
| 9,707,097 B2 | 7/2017 | Shea et al. |
| 9,730,742 B2 | 8/2017 | Lewis et al. |
| 2002/0058939 A1 | 5/2002 | Wagner et al. |
| 2004/0019353 A1 | 1/2004 | Freid et al. |
| 2004/0030339 A1 | 2/2004 | Wack et al. |

(56) References Cited

U.S. PATENT DOCUMENTS

| | | |
|---|---|---|
| 2004/0087952 A1 | 5/2004 | Borgstrom et al. |
| 2004/0176772 A1 | 9/2004 | Zubok et al. |
| 2004/0204712 A1 | 10/2004 | Kolb et al. |
| 2005/0049594 A1 | 3/2005 | Wack et al. |
| 2005/0059970 A1 | 3/2005 | Kolb |
| 2005/0107796 A1 | 5/2005 | Gerlach et al. |
| 2005/0267474 A1 | 12/2005 | Dalton |
| 2006/0015104 A1 | 1/2006 | Dalton |
| 2006/0149265 A1 | 7/2006 | James et al. |
| 2006/0235399 A1 | 10/2006 | Carls et al. |
| 2007/0055248 A1 | 3/2007 | Zlowodzki et al. |
| 2007/0142921 A1 | 6/2007 | Lewis et al. |
| 2007/0142922 A1 | 6/2007 | Lewis et al. |
| 2007/0162147 A1 | 7/2007 | Lewis et al. |
| 2007/0225715 A1 | 9/2007 | Deffenbaugh et al. |
| 2008/0119895 A1 | 5/2008 | Manceau |
| 2008/0147124 A1 | 6/2008 | Haidukewych et al. |
| 2008/0208259 A1 | 8/2008 | Gilbert et al. |
| 2008/0275510 A1 | 11/2008 | Schonhardt et al. |
| 2008/0300637 A1* | 12/2008 | Austin ............ A61B 17/8605 606/290 |
| 2009/0048605 A1 | 2/2009 | Yurek |
| 2009/0125067 A1 | 5/2009 | Mazzuca et al. |
| 2009/0143824 A1 | 6/2009 | Austin et al. |
| 2009/0171399 A1 | 7/2009 | White et al. |
| 2009/0182383 A1 | 7/2009 | Prybyla et al. |
| 2009/0192549 A1 | 7/2009 | Sanders et al. |
| 2009/0254124 A1 | 10/2009 | Bickley et al. |
| 2009/0254126 A1 | 10/2009 | Orbay et al. |
| 2009/0264936 A1 | 10/2009 | Gonzalez-Hernandez et al. |
| 2009/0292318 A1 | 11/2009 | White et al. |
| 2010/0211112 A1 | 8/2010 | Kuster et al. |
| 2010/0312286 A1 | 12/2010 | Dell'Oca |
| 2011/0015681 A1 | 1/2011 | Elsbury |
| 2011/0071572 A1 | 3/2011 | Sixto et al. |
| 2011/0071573 A1 | 3/2011 | Sixto et al. |
| 2011/0190904 A1 | 8/2011 | Lechmann et al. |
| 2011/0224737 A1 | 9/2011 | Lewis et al. |
| 2011/0238122 A1 | 9/2011 | Gradl |
| 2011/0282394 A1 | 11/2011 | Wagner et al. |
| 2011/0319943 A1 | 12/2011 | Donahoe et al. |
| 2012/0016365 A1 | 1/2012 | Freid et al. |
| 2012/0089144 A1 | 4/2012 | Murner et al. |
| 2012/0323284 A1 | 12/2012 | Baker et al. |
| 2013/0197588 A1 | 8/2013 | Abdou |
| 2013/0274813 A1 | 10/2013 | Mathieu et al. |
| 2013/0282127 A1 | 10/2013 | Gray |
| 2013/0345813 A1 | 12/2013 | Frank et al. |
| 2014/0207194 A1 | 7/2014 | Wolter |
| 2014/0214093 A1 | 7/2014 | Courtney et al. |
| 2014/0222086 A1 | 8/2014 | Kuster |
| 2014/0228892 A1 | 8/2014 | Cummins |
| 2014/0271028 A1 | 9/2014 | Arnett |
| 2014/0296923 A1 | 10/2014 | Kay et al. |
| 2015/0039038 A1 | 2/2015 | Eckhof et al. |
| 2015/0051651 A1 | 2/2015 | Terrill et al. |
| 2015/0066095 A1 | 3/2015 | Austin et al. |
| 2015/0094764 A1 | 4/2015 | Konieczynski et al. |
| 2015/0094773 A1 | 4/2015 | Clasbrummel et al. |
| 2015/0100089 A1 | 4/2015 | Richelsoph et al. |
| 2015/0100094 A1 | 4/2015 | Milz et al. |
| 2015/0105829 A1 | 4/2015 | Laird |
| 2015/0112395 A1 | 4/2015 | Day et al. |
| 2015/0142063 A1 | 5/2015 | Austin et al. |
| 2015/0150609 A1 | 6/2015 | Perrow et al. |
| 2015/0196333 A1 | 7/2015 | Austin et al. |
| 2015/0216572 A1 | 8/2015 | Ziolo et al. |
| 2015/0320455 A1 | 11/2015 | Jacene et al. |
| 2015/0351816 A1 | 12/2015 | Lewis et al. |
| 2015/0359575 A1 | 12/2015 | Pech et al. |
| 2016/0015523 A1 | 1/2016 | Lewis et al. |
| 2016/0058481 A1 | 3/2016 | Blain et al. |
| 2016/0089191 A1 | 3/2016 | Pak et al. |
| 2016/0128745 A1 | 5/2016 | Sidebotham et al. |
| 2016/0128746 A1 | 5/2016 | Dunaway |
| 2016/0166294 A1 | 6/2016 | Schneider |
| 2016/0166295 A1 | 6/2016 | Ziolo |
| 2016/0166296 A9 | 6/2016 | Juchno et al. |
| 2016/0166298 A1 | 6/2016 | Mighell et al. |
| 2016/0192968 A1 | 7/2016 | Chan et al. |
| 2016/0242925 A1 | 8/2016 | Terrell et al. |
| 2016/0270831 A1 | 9/2016 | Perrow et al. |
| 2016/0310184 A1 | 10/2016 | Kazanovicz et al. |
| 2016/0317199 A1 | 11/2016 | Hartdegen et al. |
| 2016/0317205 A1 | 11/2016 | Baker |
| 2016/0317321 A1 | 11/2016 | McDonough et al. |
| 2016/0324652 A1 | 11/2016 | Brow |
| 2016/0324657 A1 | 11/2016 | Walkenhorst et al. |
| 2016/0324662 A1 | 11/2016 | McDonough et al. |
| 2016/0333920 A1 | 11/2016 | Arnett |
| 2016/0346021 A1 | 12/2016 | Rathbun et al. |
| 2016/0361097 A1 | 12/2016 | Richelsoph et al. |
| 2017/0014168 A1 | 1/2017 | Black |
| 2017/0042587 A1 | 2/2017 | Perrow et al. |
| 2017/0042595 A1 | 2/2017 | Terrill et al. |
| 2017/0056081 A1 | 3/2017 | Langdale et al. |
| 2017/0056204 A1 | 3/2017 | Gray et al. |
| 2017/0079692 A1 | 3/2017 | Cirier et al. |
| 2017/0095282 A1 | 4/2017 | Ducharme et al. |
| 2017/0119443 A1 | 5/2017 | Cawley et al. |
| 2017/0156776 A1 | 6/2017 | Weiman et al. |
| 2017/0156887 A1 | 6/2017 | Zubok et al. |
| 2017/0164987 A1 | 6/2017 | Dominik et al. |
| 2017/0189077 A1 | 7/2017 | Blain |
| 2017/0209194 A1 | 7/2017 | Ricker et al. |
| 2017/0215930 A1 | 8/2017 | Lauf et al. |
| 2017/0224388 A1 | 8/2017 | Walker et al. |
| 2017/0238974 A1 | 8/2017 | Konieczynski et al. |
| 2017/0238979 A1 | 8/2017 | Laird |
| 2017/0265915 A1 | 9/2017 | Langdale et al. |
| 2018/0049788 A1 | 2/2018 | Rutledge et al. |
| 2018/0085153 A1 | 3/2018 | Kuster et al. |

FOREIGN PATENT DOCUMENTS

| | | |
|---|---|---|
| AU | 2010248816 A1 | 12/2011 |
| AU | 2014306747 A1 | 4/2016 |
| CA | 2511760 A1 | 6/2004 |
| CA | 2681334 A1 | 9/2008 |
| CA | 2616798 C | 1/2014 |
| CA | 2920883 A1 | 2/2015 |
| CN | 102695476 A | 9/2012 |
| CN | 105555213 A | 5/2016 |
| DE | 4343117 A1 | 6/1995 |
| DE | 102005042766 B4 | 8/2009 |
| DE | 202010005260 U1 | 6/2010 |
| DE | 102010042930 A1 | 4/2012 |
| DE | 102010048052 B4 | 6/2015 |
| DE | 102015001296 B4 | 5/2018 |
| DE | 102013013138 B4 | 8/2018 |
| EP | 1250892 A2 | 10/2002 |
| EP | 1336383 A1 | 8/2003 |
| EP | 1649819 A1 | 4/2006 |
| EP | 1741397 A2 | 1/2007 |
| EP | 1776928 A2 | 4/2007 |
| EP | 1878394 A2 | 1/2008 |
| EP | 1919385 A2 | 5/2008 |
| EP | 2175784 A2 | 4/2010 |
| EP | 2182870 A2 | 5/2010 |
| EP | 2319437 A1 | 5/2011 |
| EP | 2370012 A1 | 10/2011 |
| EP | 2477573 A2 | 7/2012 |
| EP | 2614787 A1 | 7/2013 |
| EP | 2866706 A1 | 5/2015 |
| EP | 2954870 A2 | 12/2015 |
| EP | 3033018 A2 | 6/2016 |
| EP | 3082632 A1 | 10/2016 |
| EP | 3178423 A1 | 6/2017 |
| EP | 3185794 A1 | 7/2017 |
| EP | 3284426 A1 | 2/2018 |
| EP | 3284427 A1 | 2/2018 |
| FR | 2827504 A1 | 1/2003 |
| GB | 2521346 A | 6/2015 |
| GB | 2542350 A | 3/2017 |

(56) References Cited

FOREIGN PATENT DOCUMENTS

| | | |
|---|---|---|
| JP | 5270339 B2 | 8/2013 |
| JP | 5346316 B2 | 11/2013 |
| JP | 2016165488 A | 9/2016 |
| JP | 6077069 B2 | 2/2017 |
| WO | 9639975 A1 | 12/1996 |
| WO | 2005112802 A1 | 12/2005 |
| WO | 2006113257 A1 | 10/2006 |
| WO | 2007014192 A2 | 2/2007 |
| WO | 2007014279 A2 | 2/2007 |
| WO | 2008055648 A2 | 5/2008 |
| WO | 2008077137 A1 | 6/2008 |
| WO | 2008115318 A1 | 9/2008 |
| WO | 2009017656 A2 | 2/2009 |
| WO | 2009025841 A1 | 2/2009 |
| WO | 2009042511 A1 | 4/2009 |
| WO | 2009043827 A1 | 4/2009 |
| WO | 2009134426 A2 | 11/2009 |
| WO | 2010065666 A1 | 6/2010 |
| WO | 2010076977 A2 | 7/2010 |
| WO | 2010132830 A2 | 11/2010 |
| WO | 2013167895 A1 | 11/2013 |
| WO | 2014066351 A1 | 5/2014 |
| WO | 2014168714 A1 | 10/2014 |
| WO | 2015020789 A1 | 2/2015 |
| WO | 2015023663 A3 | 4/2015 |
| WO | 2015095126 A1 | 6/2015 |
| WO | 2015100304 A1 | 7/2015 |
| WO | 2016061614 A1 | 4/2016 |
| WO | 2016172142 A1 | 10/2016 |
| WO | 2017035302 A1 | 3/2017 |

OTHER PUBLICATIONS

Extended European Search Report including Written Opinion for EP19160352.1 dated Jul. 18, 2019.
Extended European Search Report including the Written Opinion for Application No. EP 19194708.4 dated May 20, 2020, 8 pages.

* cited by examiner

BONE PLATES AND ASSOCIATED SCREWS

CROSS-REFERENCE TO RELATED APPLICATIONS

The present application is a continuation of U.S. application Ser. No. 16/289,826, filed on Mar. 1, 2019, which claims the benefit of the filing date of U.S. Provisional Patent Application No. 62/637,695 filed on Mar. 2, 2018, the disclosure of which is hereby incorporated herein by reference.

BACKGROUND OF THE INVENTION

The present disclosure relates to a bone plating system and methods of use thereof for the fixation of fractures of the bone, particularly in long bones, such as the femur, tibia, humerus and radius. More specifically, the present disclosure includes a bone plate system including a plate with screw holes adapted to receive both locking and non-locking screws and permit placement of those screws at various angles.

When a bone is damaged or fractured, bone plates are commonly attached to the outside surface of the damaged bone to stabilize the area and promote healing of the bone. Generally, the plates have a bone contacting side and a side facing away from the bone with a plurality of holes extending through the two surfaces. The holes are typically threaded for use with locking screws or non-threaded for use with non-locking, compression screws. Depending upon certain factors, such as bone quality and type, it may be more beneficial to utilize one type of screw over the other. Of course, the placement of dedicated locking and non-locking holes in the plate limits where such screws can be utilized. Moreover, certain types of holes, especially threaded holes, facilitate placement of a screw along only the axis of the hole.

There exists a need for holes that can receive both locking and compression screws in placed at various angles with respect to the axis of the hole to provide surgeons with additional options for securing the bone plate to the bone and thereby fixing the fracture.

BRIEF SUMMARY OF THE INVENTION

The present disclosure generally relates to bone plating systems for receiving locking screws in polyaxial orientations.

According to one aspect of the disclosure, a bone plate includes a bone-contacting surface, an upper surface opposite the bone-contacting surface, and a hole having a circumference and extending from the upper surface to the bone-contacting surface. The hole includes a first portion having a plurality of substantially parallel lips, each lip extends around the circumference of the hole and defines a diameter of the hole. The diameters of the hole, as defined by the lips, decrease in a direction from the upper surface to a center of the hole and increase in a direction from the center of the hole toward the bone-contacting surface.

Other embodiments according to the first aspect may include each lip extending along a plane that is substantially perpendicular to a central axis of the hole. The hole may have a second portion that extends from the upper surface to the first portion, and a third portion that extends from the bone-contacting surface to the first portion, the second and third portions having substantially frusto-conically shaped cross-sections. The second and third portions may be devoid of lips. The diameter of the hole may be smallest at about the center of the hole. Each lip may have a rounded cross-section.

According to another aspect of the present disclosure, a bone plating system includes a bone plate that has a hole that has a circumference and extends from an upper surface to a bone-contacting surface of the bone plate. The hole includes a first portion that has a series of concentric lips. Each lip extends around the circumference of the hole and defines a diameter of the hole, the diameters of the hole as defined by the lips decrease in a direction from the upper surface to a center of the hole and increase in a direction from the center of the hole toward the bone-contacting surface. The bone plating system includes a locking screw receivable within the hole of the plate in polyaxial orientations. The screw has a threaded head and a frusto-conical profile. The threads of the head are configured to engage the lips of the hole to lock the screw to the plate.

Other embodiments of this aspect may include the plate being formed of a first material and the screw being formed of a second material harder than the first material. The lips of the hole may be elastically deformable by the threads of the screw to secure the screw to the plate. The head of the screw may have a double-lead thread. The bone plating system may include a compression screw receivable within the hole. The locking screw may be moveable in a 30 degree Cone around a central axis of the hole. The bone plate may have a second portion extending from the upper surface to the first portion, and the compression screw may have a head sized and shaped to rest in the second portion of the hole without extending into the first portion of the hole. Adjacent threads of the head define a pitch, and adjacent lips of the hole define a pitch, the pitch of the threads may be substantially the same as the pitch of the lips.

In another aspect of the disclosure, a bone plating system includes a bone plate that has a hole having a lip for engaging an outer surface of an insert. The bone plate is formed of a first material. The bone plate includes an insert that defines an opening for receiving a locking screw and has an outer surface for engagement with the lip of the hole. The insert is formed of a second material that is harder than the first material. The bone plating system includes a locking screw receivable within the insert.

In other embodiments of this aspect, the outer surface of the insert may have threads to engage the lip. The insert may have an inner surface having threads, and the locking screw has a head having threads configured to engage the threads of the inner surface of the insert to secure the head to the insert. The threads of the inner surface of the insert may be single lead and the threads of the outer surface of the insert may be double lead. With the locking screw positioned within the opening of the insert, the locking screw and the insert may have coaxial central axes. The locking screw and insert may be configured to be arranged in polyaxial orientations with respect to a central axis of the hole. In such an arrangement, the central axes of the locking screw and the insert may be positioned at a non-zero angle with respect to the central axis of the hole. The insert may be removeable from the hole of the plate.

In another aspect of the disclosure, a method of securing a bone fracture includes the steps of placing a bone-contacting surface of a bone plate on bone, inserting a locking screw through a hole of the plate so that a shaft of the screw extends into bone and a head of the screw is positioned within the hole, rotating the locking screw such that threads of the head engage a plurality of substantially parallel lips positioned around a circumference of the hole to lock the screw to the hole. Each lip extends around the circumference of the hole and defines a diameter of the hole. The diameters of the hole as defined by the lips decrease in a direction from the upper surface to a center of the hole and increase in a direction from the center of the hole toward the bone-contacting surface.

According to other embodiments of this aspect, the head of the locking screw may have a frusto-conical shape. The bone fracture may be a peri-prosthetic fracture. The step of inserting may include inserting the screw at an angle within a 30 degree Cone with respect to a central axis of the hole. The plate may be formed of a first material and the screw may be formed of a second material harder than the first material and during the rotating step the lips of the hole deform. The method may include the step of inserting a second locking screw into a second hole, the second hole being substantially identical to the first hole, and rotating the second locking screw such that threads of the head engage a series of concentric lips positioned around a circumference of the second hole to lock the second locking screw to the second hole. The first screw may be locked at a first angle with respect to an axis of the first hole, and the second screw may be locked at a second angle with respect to an axis of the second hole, the first and second angles being different.

DETAILED DESCRIPTION

As used herein unless stated otherwise, the term "anterior" means toward the front part of the body, and the term "posterior" means toward the back part of the body. When referring to specific directions in the following discussion of a certain device, the terms "proximal" and "distal" are to be understood in regard to the device's orientation and position during exemplary application to human body. Thus, the term "proximal" means closer to the operator or in a direction toward the operator, and the term "distal" means more distant from the operator or in a direction away from the operator. In addition, the terms "about," "generally," and "substantially" are intended to mean that deviations from absolute are included within the scope of the term so modified.

Figure 6:
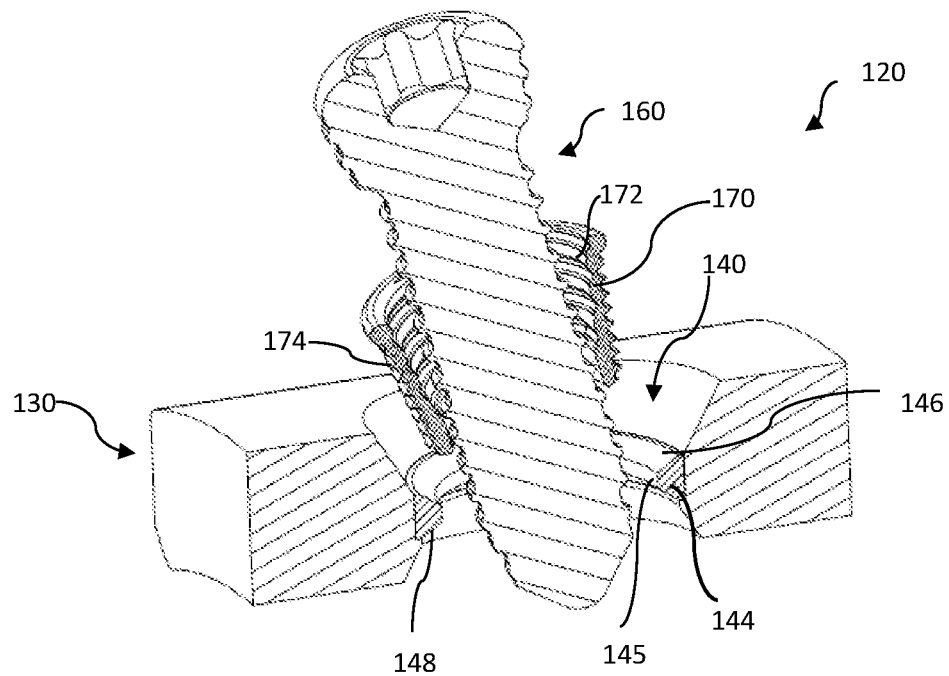
FIGS. 6 and 7 are cross-sectional views of a bone screw hole and locking screw according to another embodiment of the present disclosure.
Figure 7:
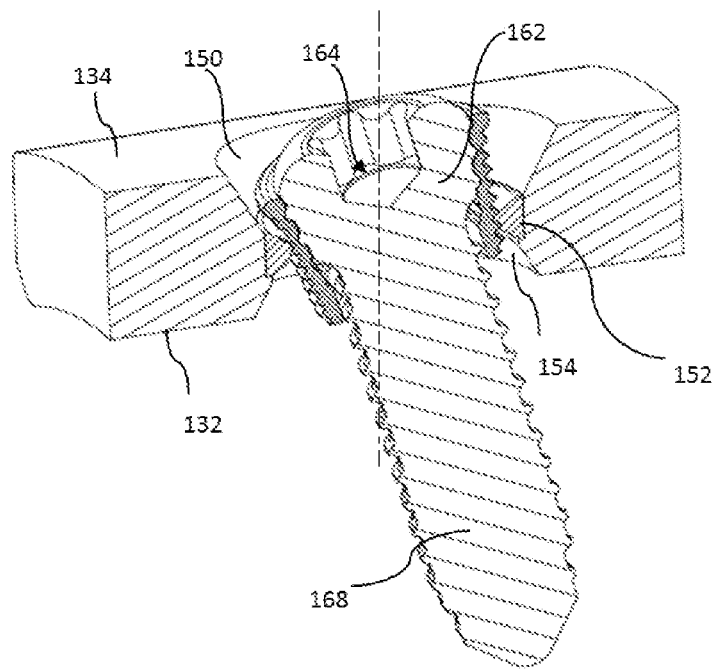

Additionally, certain of the embodiments include similar features, for which similar reference numerals are utilized, albeit within a different 100-series of numbers. For instance, FIGS. 1-5 illustrate a polyaxial screw system 20, while FIGS. 6 and 7 illustrate a system 120.

Referring to FIGS. 1-5, an embodiment of a polyaxial screw system 20 for the fixation of bone fractures according to the present disclosure is shown. System 20 includes illustrative bone plate 30 defining plate holes 40 adapted to receive locking and/or non-locking screws. Generally, embodiments of the present disclosure include bone plates that may be similar to plate 30, although each embodiment includes a different feature that enables polyaxial locking of screws within holes 40, as will be described in further detail below. Further, each of the bone plates of the present disclosure may receive locking screws, compression screws, or a combination of both in the plurality of polyaxial holes 40. Although one type and/or shape of plate 30 is shown herein, and such plate may indeed be novel and unobvious in view of the prior art, it is to be understood that plates according to the present invention can be designed for use on various bones and thusly can be any configuration necessary for such use. Indeed, certain plate sizes and shapes are well known for certain applications and the different hole configurations noted below can be utilized therewith.

In the illustrated embodiment, plate 30 includes bone-contacting surface 32 and upper surface 34 opposite the bone-contacting surface. In an implanted configuration, bone-contacting surface 32 is positioned on the bone and upper surface 34 is substantially opposite to the bone-contacting surface. Generally, throughout the various embodiments of the present disclosure, the term "inferior" means toward the bone-contacting surface and the term "superior" means toward the upper surface.

Plate 30 defines a length extending from first end 36 to second end 38. In the embodiment shown, plate 30 has a substantially constant plate thickness. First end 36 is anatomically formed to conform to the trochanter region of the femur. In particular, in an implanted state, first end 36 conforms to the convex surface of the femur in the region of the greater trochanter. Second end 38 is anatomically formed to conform to the condyle region, in particular the convex surface of the femur in the region of the medial condyle. As such, plate 30 provides conformity both in the trochanter region and in the condyle region of the femur, without requiring intense contouring when fixing the plate to the femur. In another embodiment, the plate thickness may vary along the length of the plate. Plate 30 may be formed from a single piece of rigid material, such as stainless steel, titanium and its alloys.

Figures 1, 2:
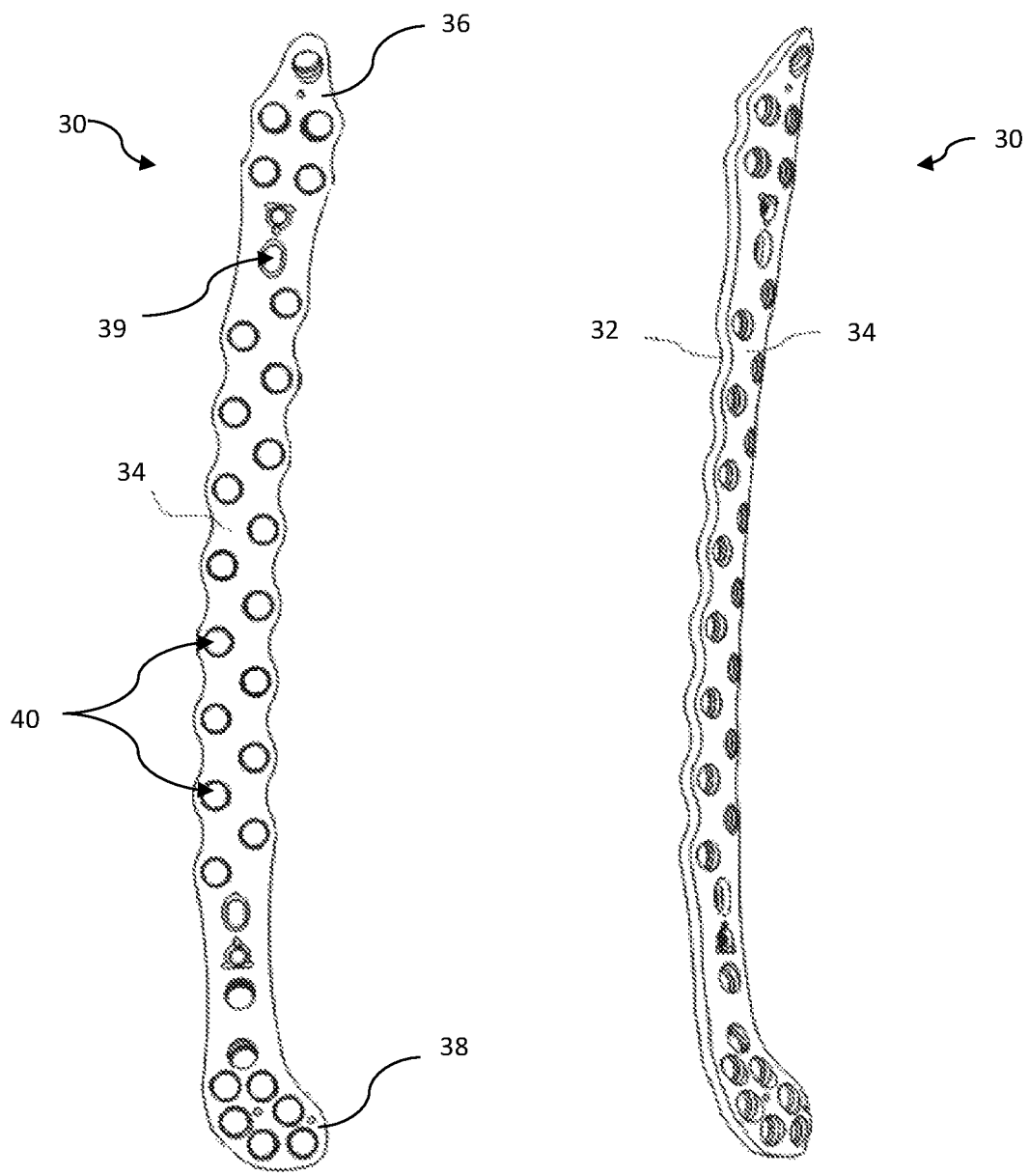
FIG. 1 shows a top view of an illustrative bone plate according to an embodiment of the present disclosure.
FIG. 2 shows a perspective side view of the bone plate of FIG. 1.

As shown in FIGS. 1 and 2, plate 30 may include at least one oblong hole 39 extending from bone-contacting surface 32 to upper surface 34 for receiving a non-locking screw. Oblong hole 39 may have a length extending in the same direction as the length of plate 30 and preferably acts in conjunction with the non-locking screw to compress a fracture, such as a peri-prosthetic fracture. Plate 30 also includes a plurality of holes 40 extending from bone-contacting surface 32 to upper surface 34. Holes 40 are circular, although in other embodiments the holes may have a different shape. Holes 40 are configured to accept locking and non-locking screws and at varying angles with respect to an axis formed through the hole, shown in FIG. 5. In other words, the holes include a polyaxial locking feature. Generally, embodiments of the present disclosure include bone plates that may be similar to plate 30, although each embodiment includes a different feature that enables polyaxial locking of screws within holes 40, as will be described in further detail below. Although holes 40 are described herein with connection to plate 30, the holes may be employed on a bone plate having any shape, and the bone plate shown in FIGS. 1-2 is not meant to be limiting.

Figure 3:
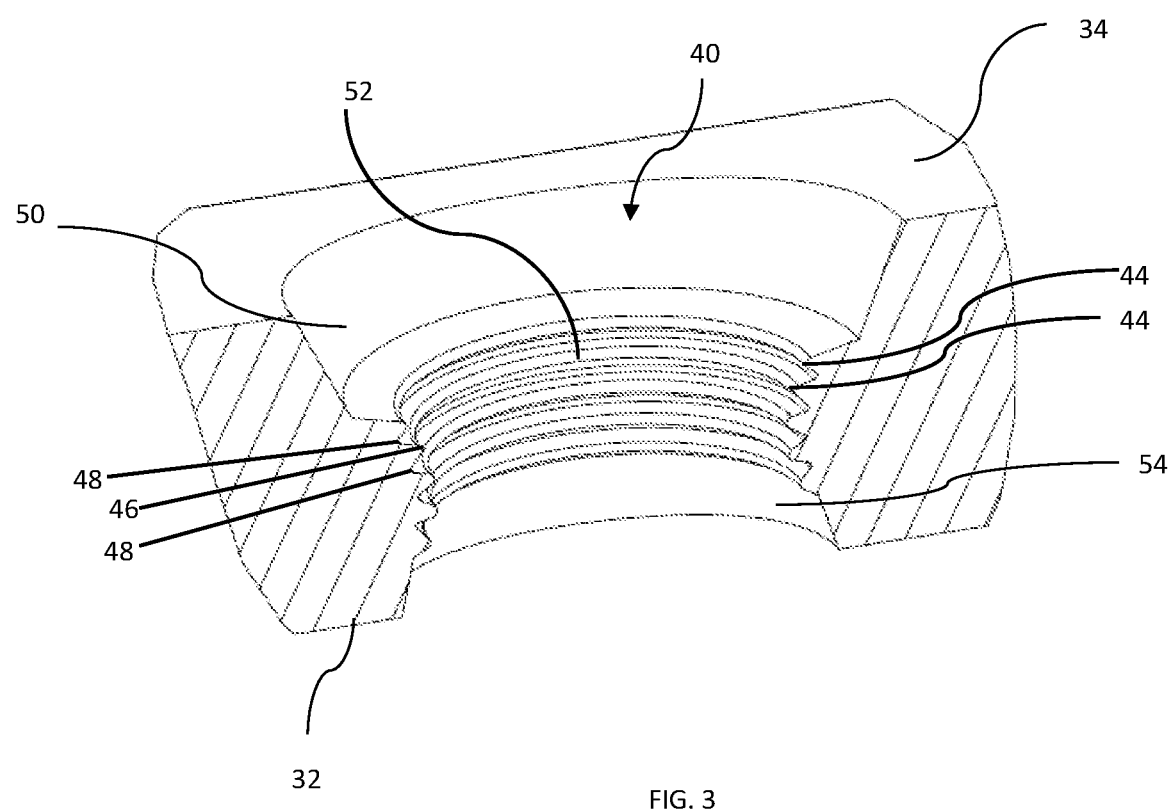
FIG. 3 shows a cross-sectional view of a hole of the bone plate of FIG. 1 according to an embodiment of the present disclosure.
Figure 4:
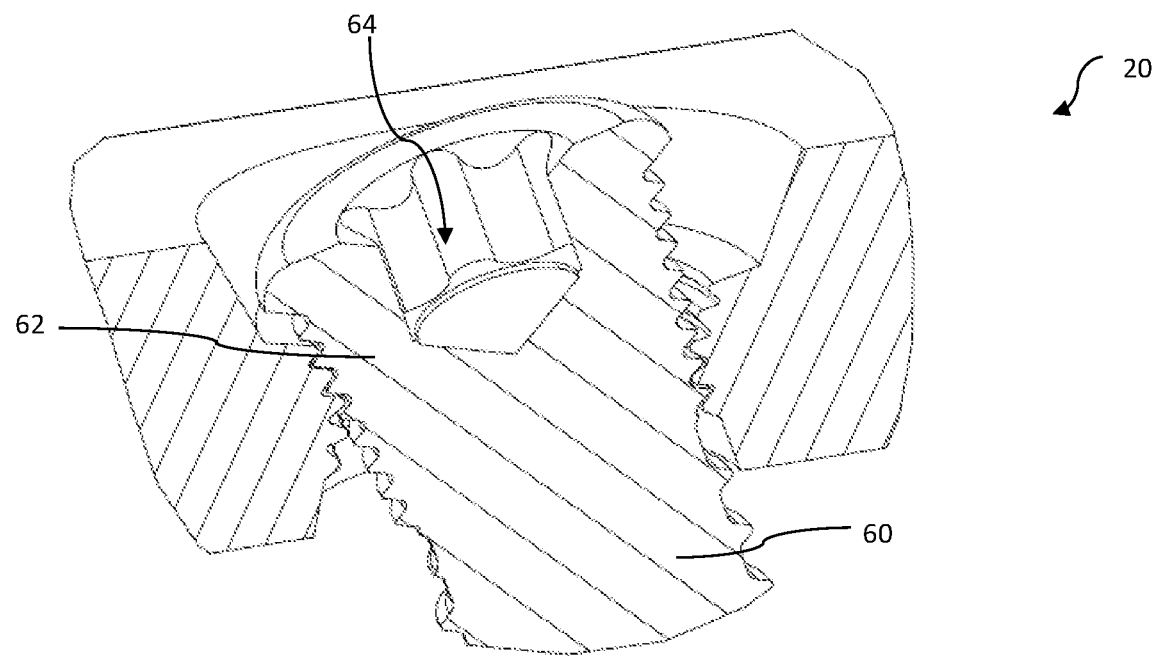
FIG. 4 shows a cross-sectional view of the hole of FIG. 3 and a locking screw according to an embodiment of the present disclosure.

FIGS. 3 and 4 show enlarged cross-sectional views of one of the holes 40 of plate 30. Hole 40 extends along a central hole axis that is substantially perpendicular to bone-contacting and upper surfaces 32, 34, respectively. Hole 40 includes central portion 52 formed of a plurality of non-threaded lips 44 extending around the circumference of the hole, such that each lip completes a revolution around the hole. Each lip 44 defines a specific diameter of the hole. For example, a superior-most lip defines a first diameter of the hole, and the lip adjacent the superior-most lip defines a second diameter of the hole different than the first diameter. As shown, these diameters decrease towards the middle of the hole and increase again towards the bottom of the hole so as to create a substantially curved cross-section in the interior of the hole. Lips 44 are substantially parallel and concentric to one another, and each lip is substantially perpendicular to the central axis of the hole. In the illustrated embodiment, each lip 44 has a round cross-section, although in alternative embodiments, the cross-section may be trapezoidal, triangular, or any other shape.

As shown in FIG. 3, each lip includes a crest 46 extending between two troughs 48. Central portion 52 has a substantially spherical profile, although, certain of the lips 44 may be configured such that the profile between those respective lips is tapered rather than rounded. The pitch, i.e., the distance between adjacent lips such as from crest to crest, may be substantially the same for the plurality of the lips, and at least two pairs of adjacent lips have the same pitch.

Hole 40 includes upper portion 50 extending from upper surface 34 to a superior-most lip 44 and lower portion 54 extending from bone-contacting surface 32 to an inferior-most lip 44. Hole 40 has a relatively larger diameter at upper portion 50 than at lower portion 54. Upper and lower portions 50, 54 are conically tapered and have smooth, flat surfaces and form countersinks. Upper portion 50 and lower portion 54 may taper at substantially the same or different angles or may not taper at all (i.e., extend perpendicular to the surfaces).

Figure 5:
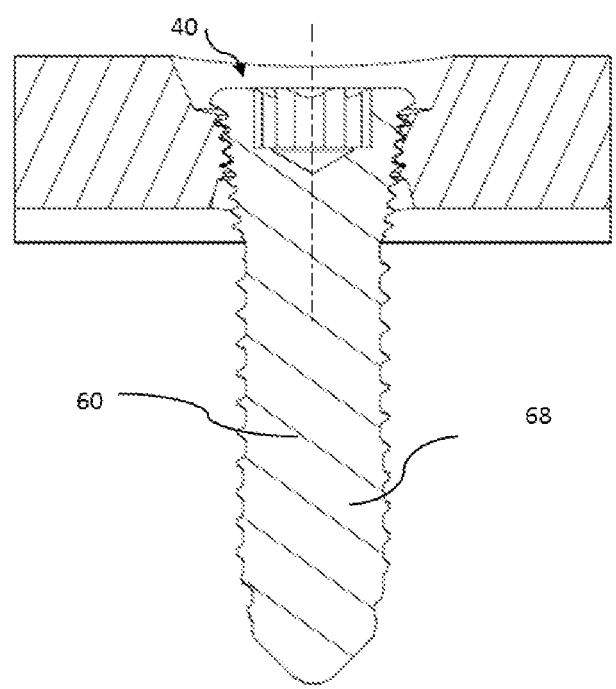
FIG. 5 is a cross-sectional side view of the system of FIG. 4, with the screw inserted at different angles.

As shown in FIGS. 4 and 5, locking screw 60 includes head 62 and shaft 68. Head 62 has a hexagonal socket 64 for mating engagement with a driving tool (not shown). Although socket 64 is shown has having a hexagonal shape, the socket can be any shape suitable for transmitting torque from a correspondingly shaped driver tool. Head 62 has a substantially frusto-conical shape and is threaded. The pitch, i.e. the distance between adjacent threads, is substantially equally to the pitch of the lips 44 of the hole 40. Head 62 may include a double entry thread, but in other embodiments, the head may include a single entry thread. Shaft 68 extends along a longitudinal axis of the screw 60 and is threaded along its length. Screw 60 may be formed from a material that is harder than the material that plate 30 is formed from. For example, screw 60 may be formed from cobalt chromium, while plate 30 may be formed of titanium and its alloys.

In use, bone-contacting surface 32 is positioned on the damaged bone. Locking screw 60 is inserted into hole 40 with head 62 positioned within and surrounded by hole 40 and shaft 68 extending through bone-contacting surface 32 and into the bone. Screw 60 may be inserted into the hole within a cone of 30 degrees with respect to an axis of the hole. For instance, FIG. 4 shows screw 60 inserted within the hole at about 15 degrees relative to the central axis of the hole, and FIG. 5 shows the screw inserted positioned at about 0 degrees relative to the central axis of the hole. With screw 60 within hole 40, the screw may be torqued. Due to the conical shape of head 62, the head applies radial forces to the bone plate 30 so that the threads of the head engage lips 44 of the hole, which results in a form fit. Because screw 60 is formed of a harder material than bone plate 30, the bone plate and lips 44 may elastically deform, locking the screw into the hole of the plate at the desired angle. Thus, plate 30 may have a plurality of holes 40, and each screw 60 may be placed at a same or different angle with respect to the axes of the bone holes.

Alternatively, a compression screw (not shown) may be inserted into hole 40 and secured to the bone. The head of such screw may rest within upper portion 50, without extending into central portion 52. As such, plate system 20 can accommodate locking screws 60, in the manner described above, as well as compression screws in holes 40. The plurality of the holes 40 of plate 30 may include all locking screws 60, or all compression screws, or a combination of both.

In another embodiment of the present disclosure, system 120 is similar in most respects with system 20. Similar reference numerals are utilized for similar features but within the 100 series of numbers, the similar features of which will not be described again. Significantly, plate 130 includes holes 140 which employ a different locking feature than holes 40 of plate 30.

As shown in FIGS. 6 and 7, system 120 includes bone plate 130 with polyaxial locking holes 140. Each hole 140 includes central portion 152 with a single lip 144 projecting inward toward a center line of the hole and extending around the circumference of the hole. Lip 144 forms a seating surface that allows for engagement and locking with locking insert 170, described in further detail below. Lip 144 includes upper tapered surface 146 and lower tapered surface 148 with central surface 145 extending between them. Upper and lower tapered surfaces 146, 148 may taper at substantially same or at different angles from one another. Central surface 145 extends in a plane substantially parallel to the central axis of hole 140 and substantially perpendicular to upper surface 134. Lip 144 may be integral with hole 140 of plate 130 so as to be manufactured as a monolithic, single piece.

Hole 140 also includes upper portion 150 extending from upper surface 134 to central portion 152 and lower portion 154 extending from bone-contacting portion 132 to central portion 152. Hole 140 has a relatively larger maximum diameter at upper portion 150 than at lower portion 154. Upper and lower portions 150, 154 are conically tapered and have smooth, flat surfaces and form countersinks. Upper portion 150 and lower portion 154 may taper at substantially the same or different angles or not taper at all.

Locking screw 160 includes head 162 and shaft 168. Head 162 has a hexagonal socket 164 for mating engagement with a driving tool (not shown). Although socket 164 is shown has having a hexagonal shape, the socket can be any shape suitable for transmitting torque from a correspondingly shaped driver tool. Head 162 is threaded and includes a male thread which may be a single entry or double entry thread. Head 162 may be frusto-conically shaped. Shaft 168 extends along a longitudinal axis of the screw 160 and is threaded along its length.

Insert 170 has a generally frusto-conical shape and includes inner surface 172 and outer surface 174, opposite the inner surface. The shape of insert 170 may be designed to match the frusto-conical shape of screw head 162, although the diameter of the insert is at least slightly larger than that of the screw head so that the insert can fit around the screw head. Inner surface 172 includes female threads that match and mate with the male threads of screw head 162. Outer surface 174 includes a double entry, sharp male thread to grip lip 144 to engage the lip and allow polyaxial locking of screw 160.

Insert 170 may be formed of a material that is harder than plate 130. For example, insert 170 may be formed of cobalt-chromium (CoCr), and plate 130 may be formed of titanium and its alloys, e.g. Ti6Al4V ELI. Screw 160 may be formed of titanium and its alloys, e.g. AxSOS 3 Titanium, although the hardness of the screw is not relevant relative to the hardness of the plate.

Prior to insertion in a patient, shaft 168 of screw 160 may be placed through insert 170 such that head 162 of the screw is surrounded by the insert. Head 162 and inner surface 172 of insert 170 have corresponding mating threads, so that the screw can be rotated and secured to the insert. In this manner, screw 160 extends in a direction along a central axis of insert 170, so that the screw and insert are co-axial. This screw-insert configuration may then be inserted into hole 140 of plate 130 during surgery. Alternatively, the insert may be positioned within the hole first, and then the screw inserted through both the insert and the hole.

During surgery, with bone-contacting surface 132 of plate 130 positioned adjacent the bone, the screw-insert configuration may be inserted into hole 140 such that shaft 168 of the screw is driven into the bone. The screw-insert configuration may be inserted in multiple angles as system 120 allows polyaxial orientations of the screw-insert configuration. As screw 160 is torqued, the threads on outer surface 174 of insert 170 engage lip 144 of hole 140. Because the insert is formed of a harder material than the hole, the lip may elastically deform to secure the screw-insert configuration at the desired angle. The screw-insert configuration is formed of separate, independent elements, although the elements may be assembled in the operating room to reduce or avoid the risk of contamination.

Like system 20, plate system 120 can accommodate locking screws 160, in the manner described above, as well as compression screws (not shown) in holes 140. The plurality of the holes 140 of plate 130 may include all locking screws 160, or all compression screws, or a combination of both.

In another embodiment, FIGS. 8-12 show bone plating system 220 of the present disclosure. That system includes a plate 230 that employs a plurality of polyaxial holes 240 that extend from upper surface 234 to bone-contacting surface 232. Hole 240 includes upper portion 250 that extends from upper surface 234 to rim 245, which extends farther radially inward toward the center of the hole than the upper portion. Rim 245 continues into central portion 252, such that the rim forms an edge between upper portion 250 and central portion 252. Central portion 252 of hole 240 includes a plurality of spaced-apart, rounded concave cavities 246. In the illustrated embodiment, the cavities are spaced-apart at about 90 degrees from each other.

Figure 8:
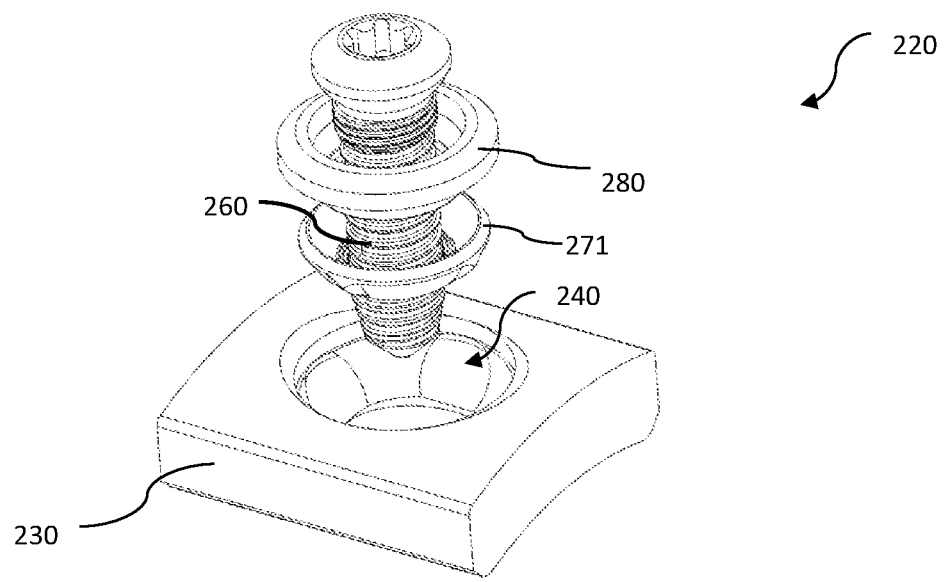
FIG. 8 is an exploded perspective top view of a bone plating system according to another embodiment of the present disclosure, with a focus on a hole and screw.
Figure 9:
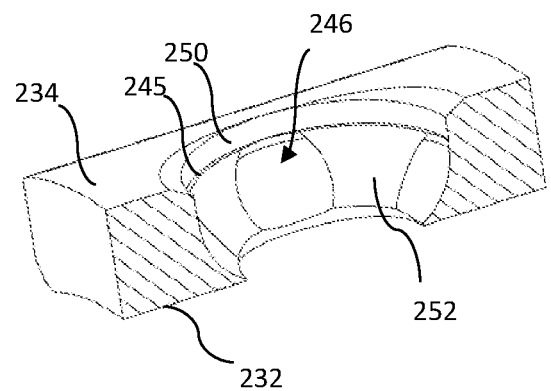
FIG. 9 is a cross-sectional view of the hole of the system of FIG. 8.
Figure 10:
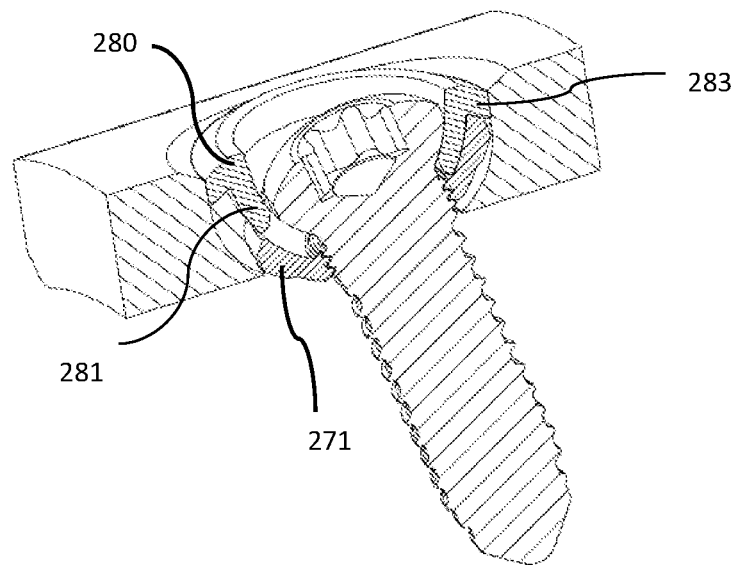
FIG. 10 is a cross-sectional view of the system of FIG. 8, with the screw inserted within the hole.
Figure 11:
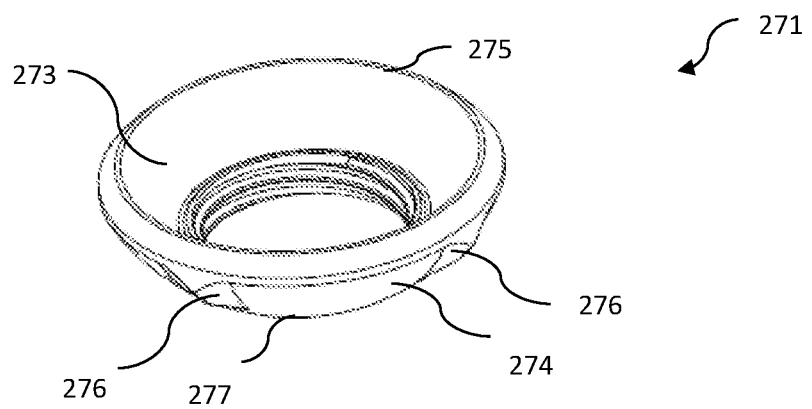
FIG. 11 are perspective top and bottom views, respectively, of a nut of the system of FIG. 8.

As shown in FIGS. 8 and 10, hole 240 is designed to accept a floating nut 271 and cap 280. Nut 271 is mounted in hole 240 and has a concave "bowl-shape" that defines a hollow interior region into which bone screw 260 can be inserted. With specific reference to FIG. 11, nut 271 includes inner surface 273 and outer surface 274, opposite the inner surface. Due to the "bowl-shape" of nut 271, it tapers gradually inward from first end 275 to second end 277. Inner surface 273 includes parallel lips at second end 277 to mate with the male threads of screw 260. Protrusions 276 extend radially outward of outer surface 274 and are spaced-apart from one another on the outer surface. Protrusions 276 are positioned relative to each other in the same manner as cavities 246 of hole 240, and accordingly, in the illustrated embodiment, the protrusions are spaced apart about 90 degrees from one another. Protrusions 276 are designed to fit within and engage cavities 246 of hole 240. Engagement of the protrusions 276 with cavities 246 of hole 240 prevent nut 271 from rotating around the hole, although the nut is freely movable in a conical motion.

System 220 further includes cap 280 welded or otherwise securely fixed within hole 240 and positioned superior to nut 271, that is the cap is closer to upper surface 234 than nut 271 is to the upper surface. With reference to FIG. 10, cap 280 includes support 281 and annular collar 283 that forms a shoulder of the cap and extends radially outward of the support. Cap 280 defines a concave interior opening into which screw 240 can be inserted. Support 281 of cap 280 has an outer diameter that is less than the inner diameter of nut 271 at first end 275 of the nut such that the support may be positioned within the nut with collar 283 forming a shoulder that abuts first end 275 of the nut, as shown in FIG. 10. Collar 283 sits within upper portion 250 of hole 240 and is secured in place by rim 245 of the hole.

Figure 12:
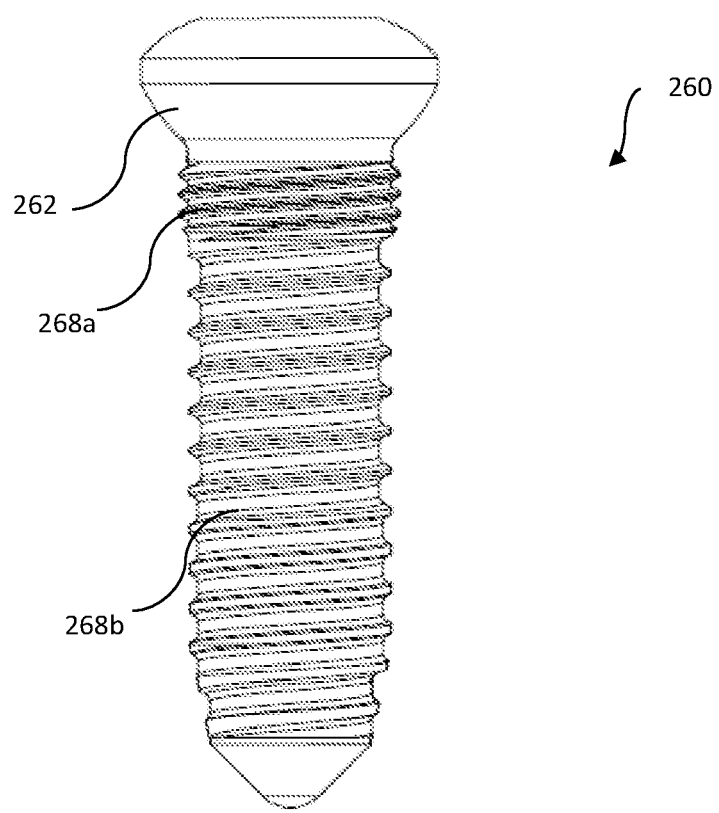
FIG. 12 is a side view of the locking screw of the system of FIG. 8.

Referring to FIG. 12, system 220 further includes screw 260 with head 262 and shaft 268 extending along a longitudinal axis of the screw. Head 262 is substantially spherically shaped, and as shown in the illustrated embodiment, the screw head is not threaded. Shaft 268 is threaded and includes top portion 268a with double lead threads and bottom portion 268b with single lead threads. The threads on top portion 268a are male threads that engage the parallel lips of nut 271 to secure the screw to the nut.

In use, screw 260 is inserted through hole 240, nut 271, and cap 280. Prior to locking the screw, nut 271 is "floating." This means that the nut has a conical range of motion within the hole and can move along the spherical surface of central portion 252, which occurs prior to the screw being torqued into a final position. The "floating" arrangement of the nut allows polyaxial orientations of the screw within the hole. As screw 260 is rotated, the male threads of top portion 268a of the screw shaft engage the parallel lips of nut 271. Protrusions 271 of nut 271 engage cavities 246 of the hole, to prevent the nut from rotating around the hole. As the spherical head 262 of the screw contacts cap 280, nut 271 is forced toward the cap causing friction between the nut and the cap to lock the screw to the plate.

In another embodiment, FIGS. 13-17 show bone plating system 320 of the present disclosure. System 320 includes bone plate 330 with a plurality of holes 340 and screws 360, each with threaded conical head 362 and threaded shaft 368. Each hole 340 includes floating washer 371 and cap 380, which is welded or otherwise securely fixed to the hole.

Figure 13:
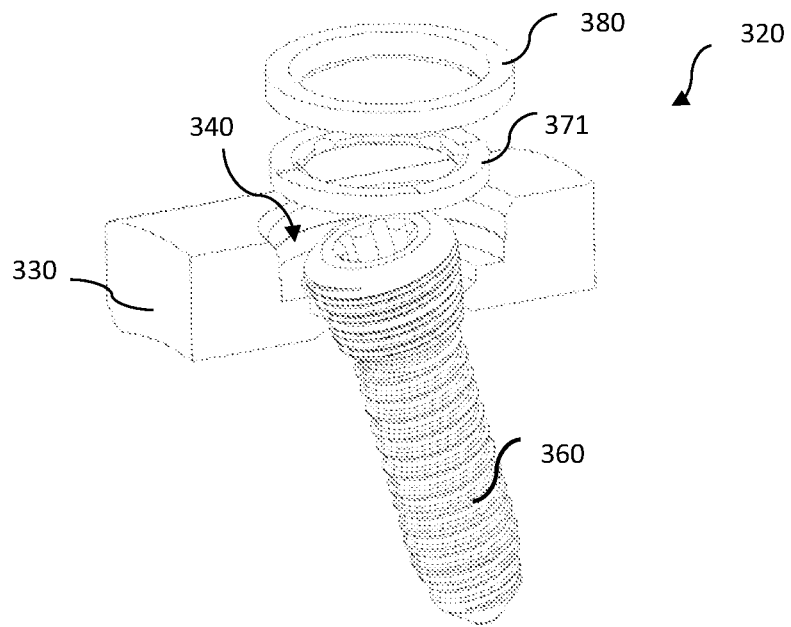
FIG. 13 is an exploded perspective top view of a bone plating system according to another embodiment of the present disclosure, with a focus on a hole and screw.
Figure 14:
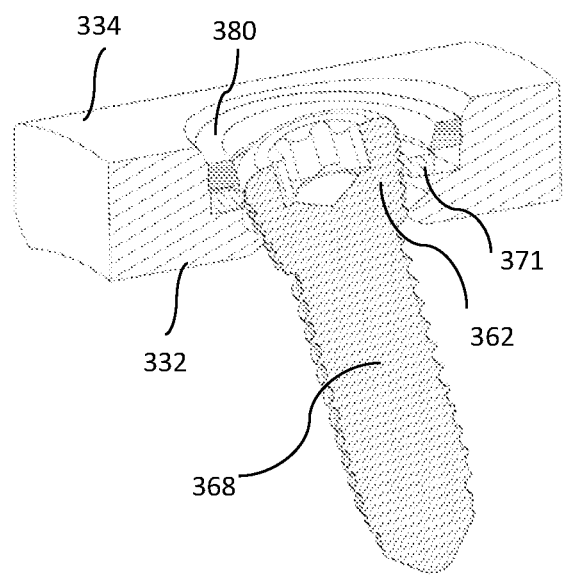
FIG. 14 is a cross-sectional view of the system of FIG. 13, with the screw inserted within the hole.
Figure 15:
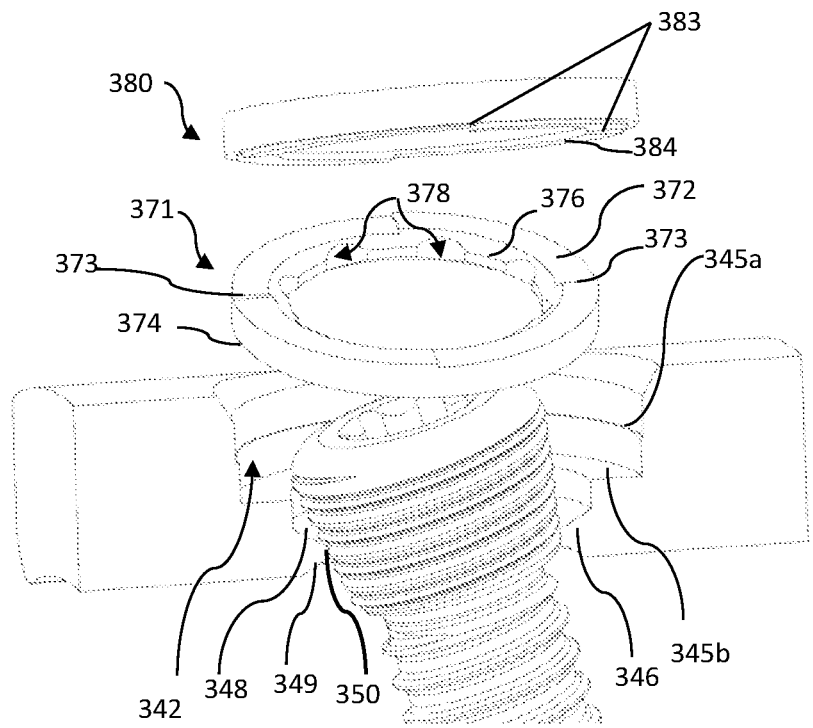
FIG. 15 is an enlarged cross-sectional view of the plate and hole and perspective views of the washer, cap and screw of the system of FIG. 13.

As shown in FIGS. 13-15, hole 340 includes an upper portion 342 that includes a stepped arrangement that defines different diameters of the hole. In the illustrated embodiment, there are two steps, a first step including flat surface 345a and a second step including flat surface 345b. Flat surfaces 345a and 345b extend around the circumference of the hole, with flat surface 345b defining a smaller diameter of the hole than flat surface 345a.

Hole 340 further includes lip 346 extending from the inferior-most step to bone-contacting surface 332. Lip 346 includes upper and lower tapered surfaces 348, 349, respectively, with central surface 350 extending between them. Upper tapered surface 348 and lower tapered surface 349 may taper at a substantially same or at different angles from one another. Central surface 350 extends in a plane substantially parallel to the central axis of hole 340 and substantially perpendicular to upper surface 334 of bone plate 330.

System 320 includes washer 371 mounted in hole 340 that has a "disc-shape" and defines an interior opening extending from upper surface 372 to lower surface 374. The distance between upper surface 372 and lower surface 374 defining a width of the washer. Upper surface 372 includes at least one ramp 373 such that the two sides of the upper surface 372 adjacent a ramp 373 are not in a continuous plane, such that the width of the washer is not uniform around its circumference. Washer 371 includes a plurality of spaced apart concave recesses 378 on inner surface 376. Washer 371 is designed to sit on lower surface 345b of the inferior-most step of hole 340.

Cap 380 is welded into hole 340 superior to washer 371, i.e. closer to upper surface 334 of bone plate 330. Cap 380 has a "disc-shape" and defines an interior opening. Cap 380 includes at least one ramp 383 on its lower surface 384 that corresponds to ramp 373 on the upper surface 372 of washer 371. Cap 380 is welded to sit on lower surface 345a of a step of hole 340.

In use, washer 371 is freely moveable along a horizontal plane but rotation of the washer is limited due to the ramps. With screw 360 inserted in hole 340 and thus through cap 380 and washer 371, a first portion of threaded screw head 362 engages washer 371 and a second portion of the screw head engages lip 346. Because washer 371 can move horizontally with respect to lip 346, the screw may be arranged at variable angles with two locking planes, i.e. a first plane extending at the point of contact of the screw head and the washer and a second plane extending at the point of contact of the screw head and the lip.

The washer may be locked at the desired angle by the rotation of screw 360. As the screw is rotated, the washer also initially rotates. However, due to the ramps, as the washer rotates, the ramps act as a wedge to lock the washer in position.

Figure 16:
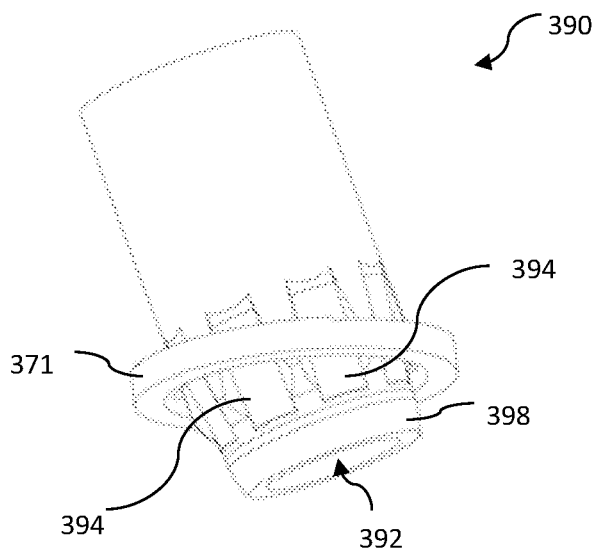
FIG. 16 shows a perspective side view of a locking key and washer of the system of FIG. 13.
Figure 17:
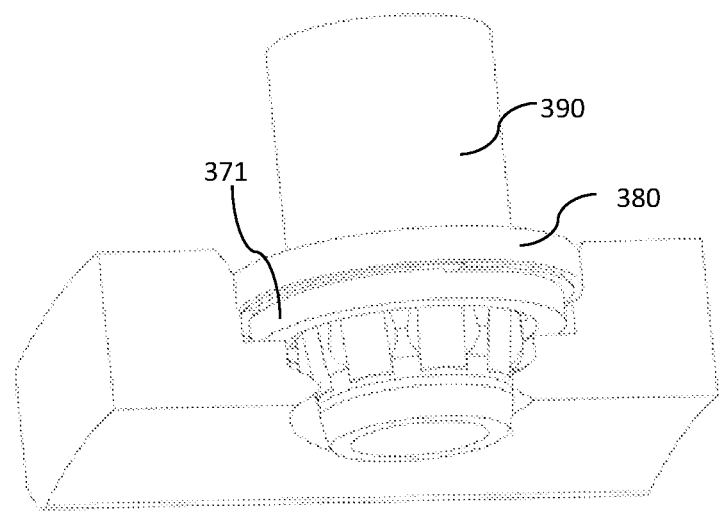
FIG. 17 is a cross-sectional view of the hole and perspective bottom views of the locking key, washer, and cap of the system of FIG. 13.
Figure 18:
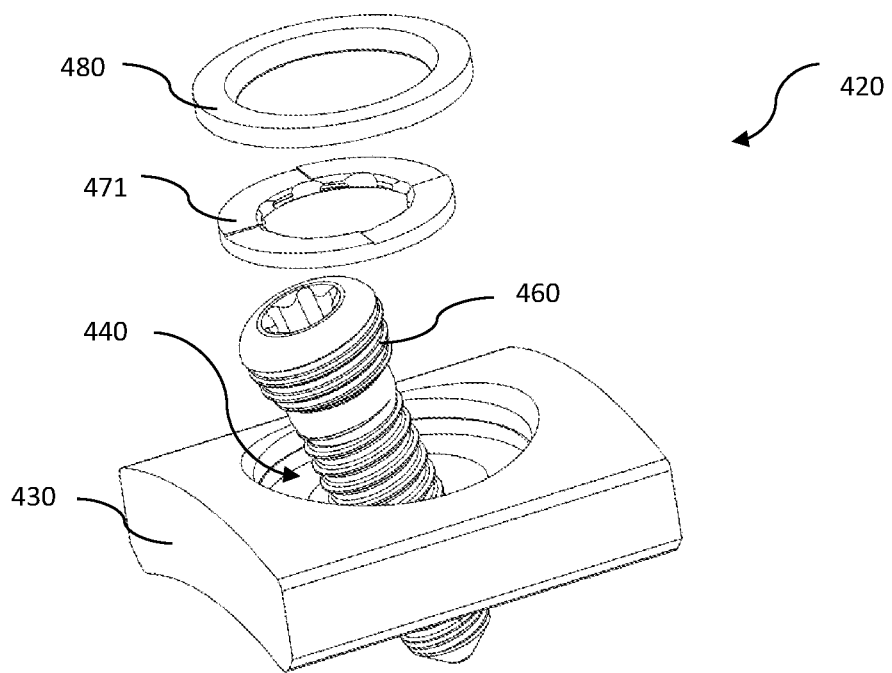
FIG. 18 is an exploded perspective top view of a bone plating system according to another embodiment of the present disclosure, with a focus on a hole and screw.
Figure 19:
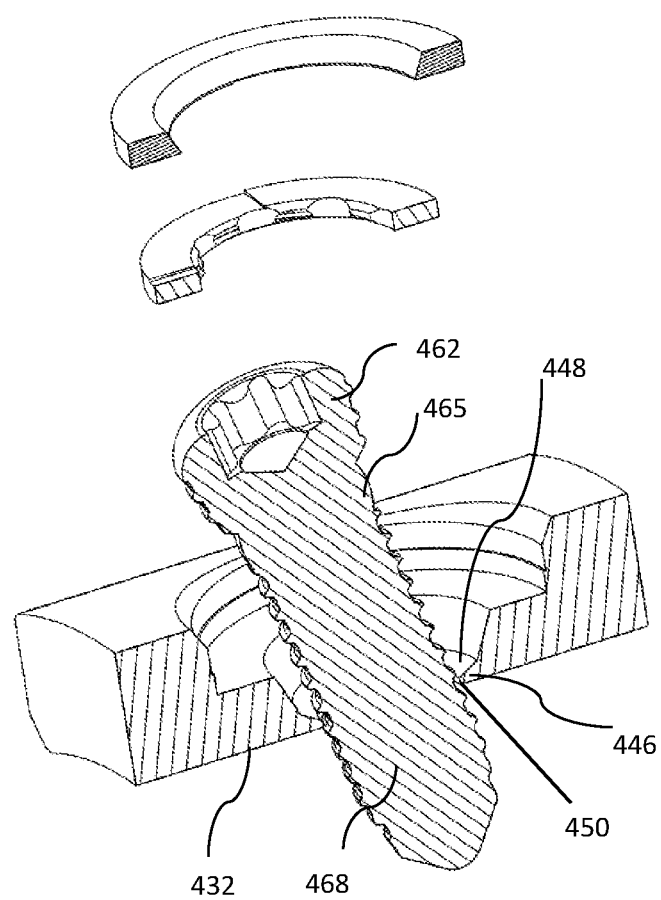
FIG. 19 shows an exploded cross-sectional view of the system of FIG. 18.
Figure 20:
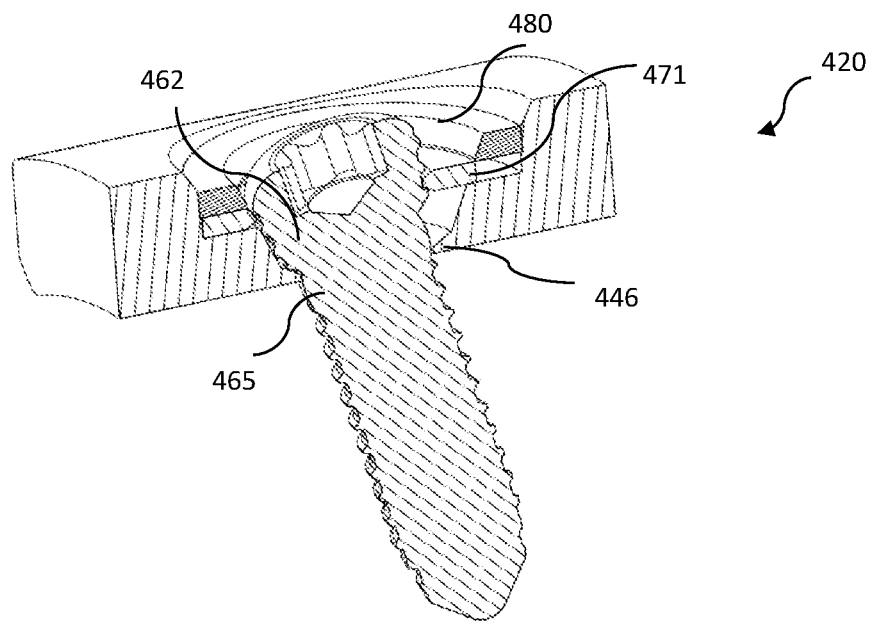
FIG. 20 is a cross-sectional view of the system of FIG. 18.
Figure 21:
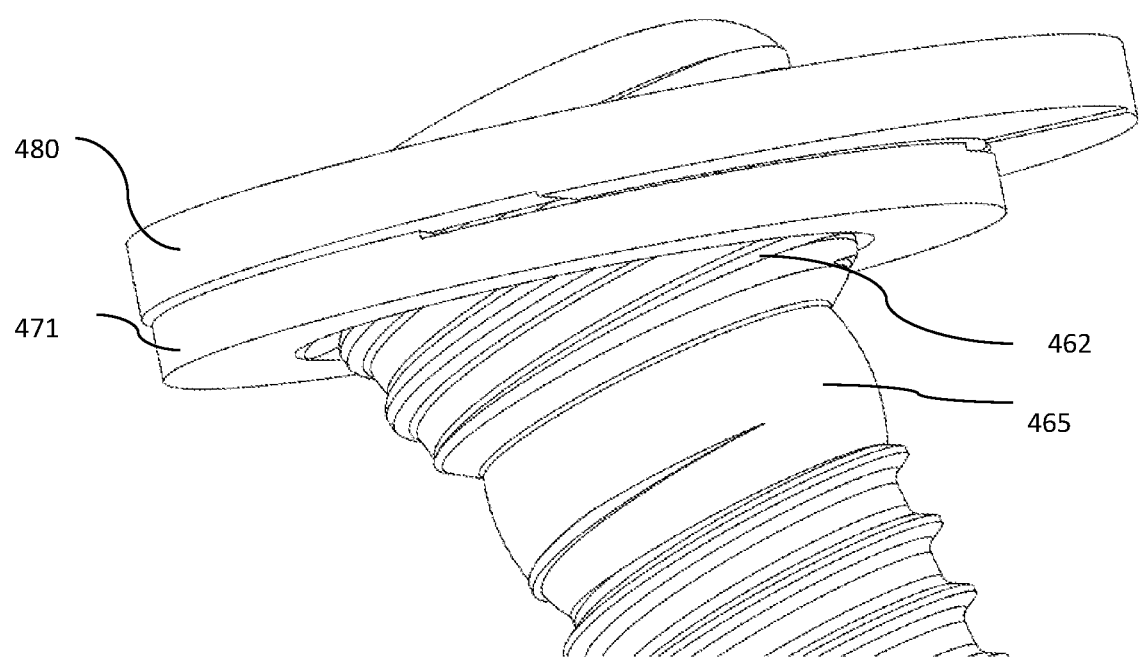
FIG. 21 is a perspective side view of the washer, cap, and proximal portion of the screw head of the system of FIG. 18.
Figure 22:
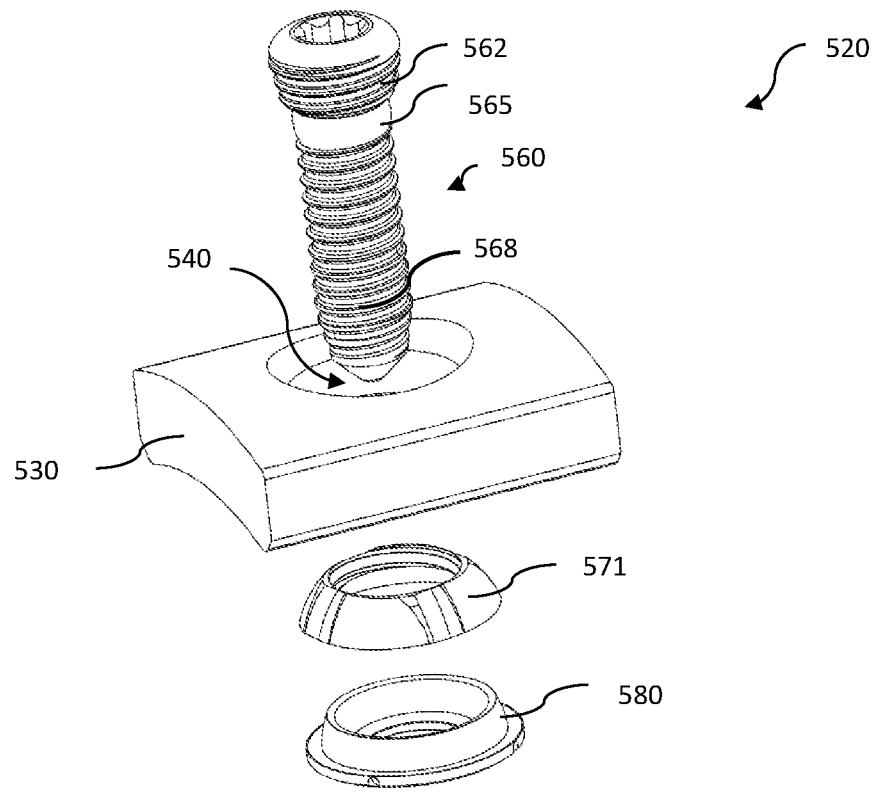
FIG. 22 is an exploded perspective top view of a bone plating system according to another embodiment of the present disclosure, with a focus on a hole and screw.

Alternatively, as shown in FIGS. 16-17, locking key 390 may be used in system 320 to fix the washer in a desired position prior to insertion of screw 360. Locking key 390 has a substantially cylindrical shape defining opening 392 extending along the longitudinal axis of the key. Locking key 390 includes projections 394 spaced apart around a circumference of the key and extending radially outward from an outer surface near end 398 of the key. Projections 394 are sized and shaped to be received within recesses 378 of the washer 371.

In use, locking key 390 is inserted through hole 340, cap 380, and washer 371. Locking key 390 may be inserted in polyaxial orientations, and as key 390 is rotated, projections 394 of locking key 390 engage recesses 378 of washer 371. Rotation of washer 371 locks the washer in the desired position, with key 390 at a desired angle within hole 340. After removal of key 390, screw 360 is inserted in hole 340 at the same angle as key 390 had been positioned. Thus, use of locking key 390 allows for polyaxial locking of screw 360.

In yet another embodiment, FIGS. 18-21 show bone plating system 420 of the present disclosure. System 420 is similar in most respects to system 320, although the system results in a single locking plane, and an additional guiding plane rather than two locking planes, as will be described below. Similar reference numerals are used for similar features, although in the 400 series.

System 420 includes a plurality of holes 440 similar to holes 340 except that hole 440 includes a partial lip 446 formed of tapered surface 448 and central surface 450 extending from bone-contacting surface 432 to tapered surface 448.

Screw 460 includes conical head 462, shaft 468, and smooth rounded transition portion 465 extending between the head and the shaft and having a substantially spherical profile. Head 462 and shaft 468 are threaded, while transition portion 465 is not.

Hole 440 of plate 430 functions similarly to hole 340, except that partial lip 446 engages non-threaded transition portion 465 of the screw to provide support to the screw but does not lock the screw along the plane of contact with the partial lip. Thus, hole 440 provides for one locking plane along washer 471, and an additional plane of support at partial lip 446.

FIGS. 22-27 show yet another embodiment of a bone plating system of the present disclosure. System 520 includes bone plate 530 with a plurality of holes 540 and screws 560 that are similar to screws 460 of bone plating system 420. In particular, screws 560 include threaded head 562, non-threaded transition portion 565, and shaft 568. Non-threaded portion 565 may be convex, concave, or cylindrically shaped, although in the illustrated embodiment, it is convex.

Figure 23:
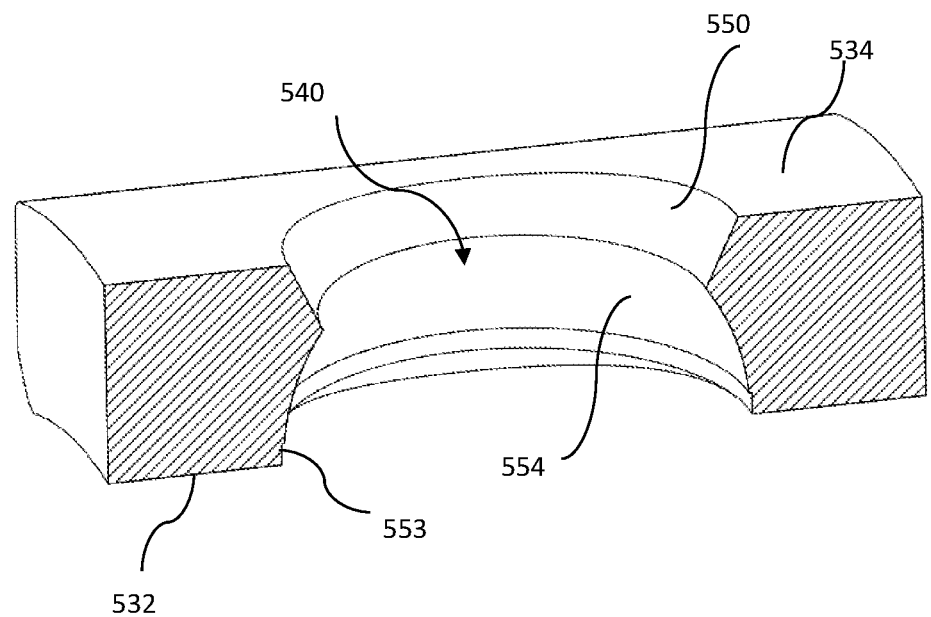
FIG. 23 is a cross-sectional view of the plate hole of the system of FIG. 22.

As shown in FIG. 23, hole 540 includes first portion 550 extending from upper surface 534 to second portion 554 that extends to third portion 553 which terminates at bone-contacting surface 532. First portion 550 has a conically inward tapering profile and second portion 554 has a substantially spherical profile. Third portion 553 tapers outwardly toward bone-contacting surface 532 or in another embodiment it may have a substantially straight profile.

As shown in FIGS. 22 and 24-27, system 520 includes "floating" nut 571 moveable within the hole and cap 580 welded or otherwise securely fixed to plate hole 540. Both cap 580 and nut 571 have openings to receive screw 560.

Figure 24:
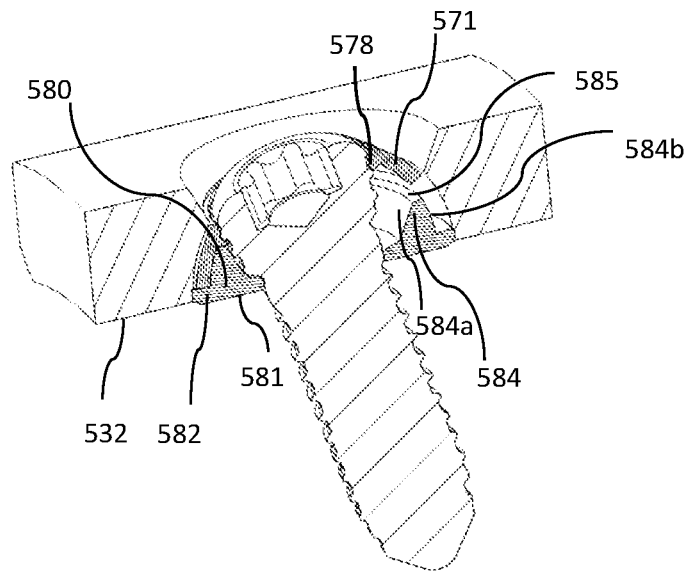
FIG. 24 is a cross-sectional view of the system of FIG. 22.
Figure 25:
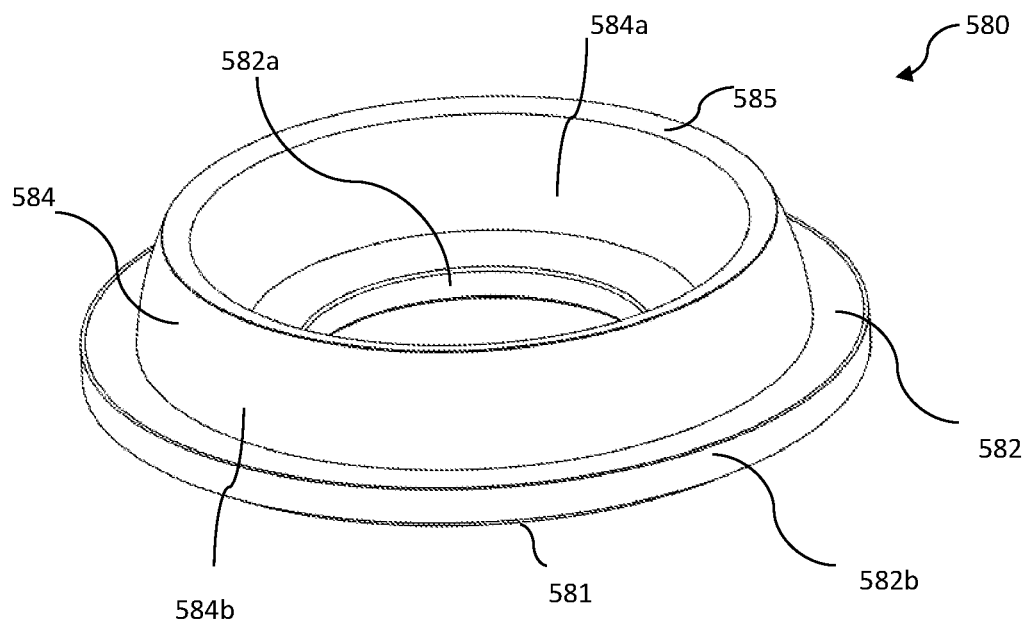
FIG. 25 is a perspective top view of the cap of the system of the FIG. 22.
Figure 26:
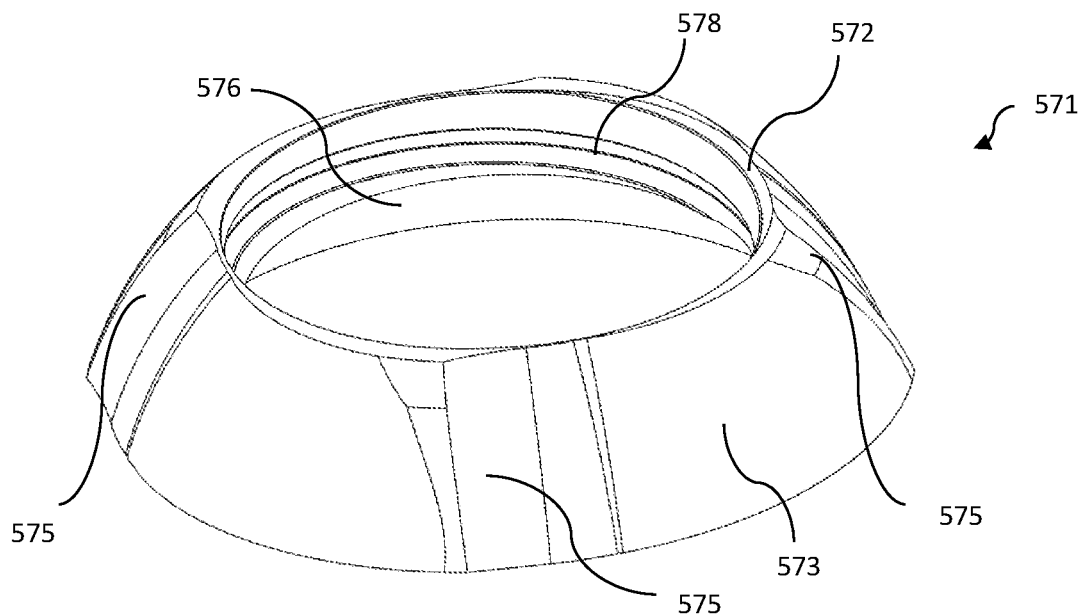
FIG. 26 is a perspective top view of the floating nut of the system of FIG. 22.
Figure 27:
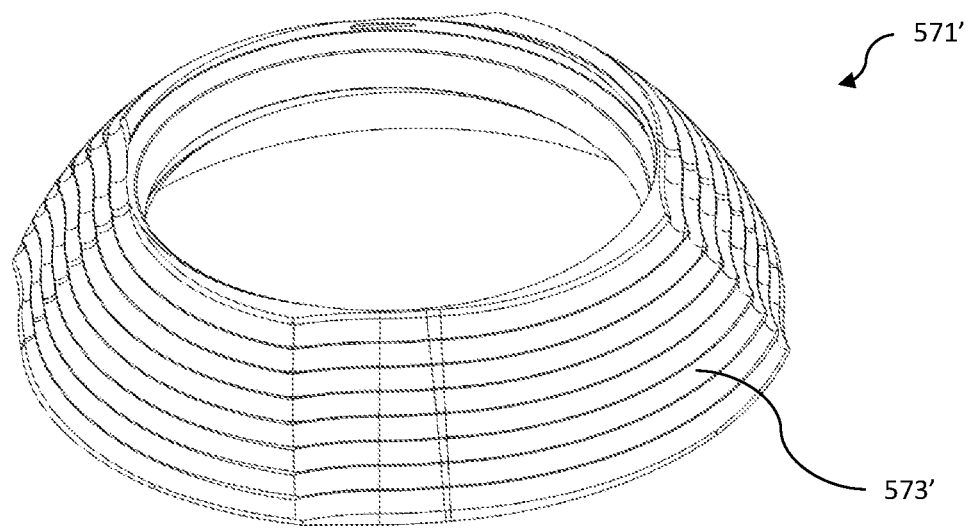
FIG. 27 is a variant of the floating nut of FIG. 26.
Figure 28:
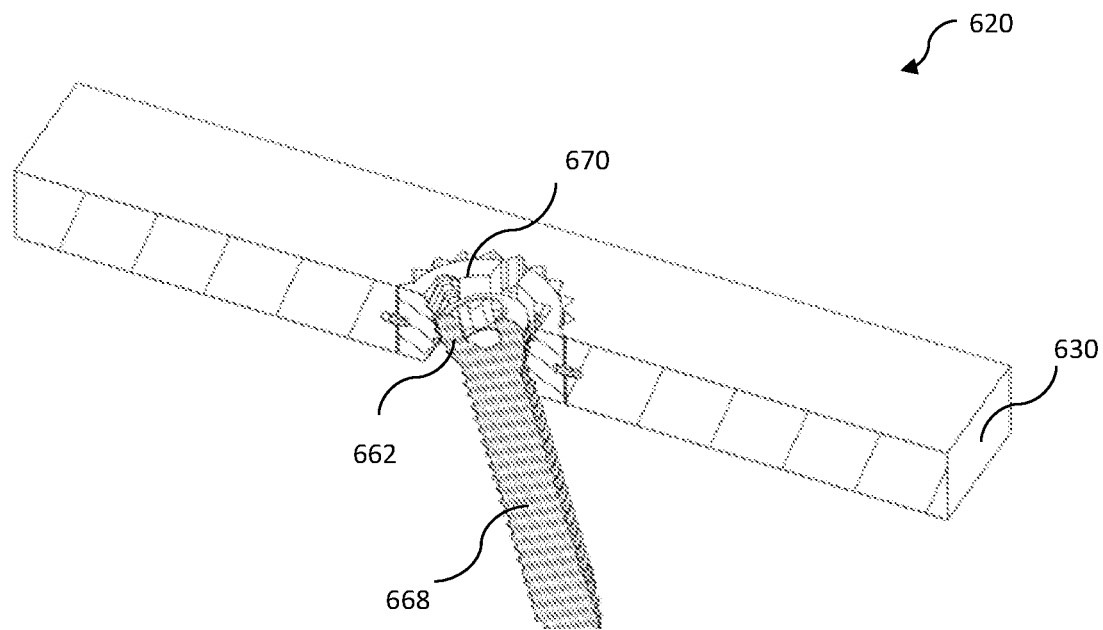
FIG. 28 is a cross-sectional top view of a bone plating system according to another embodiment of the present disclosure, with a focus on a hole and screw.
Figure 29:
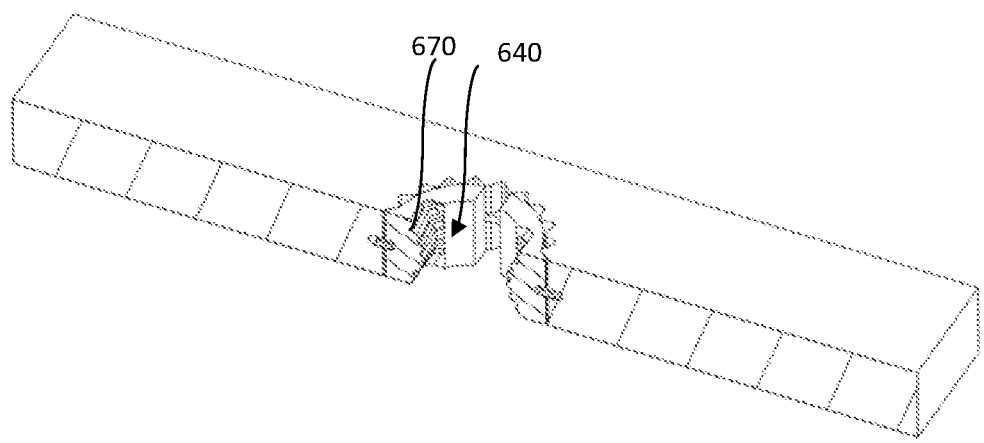
FIG. 29 is a cross-sectional view of the hole and insert of the system of FIG. 28.

As best shown in FIGS. 24 and 25, cap 580 is annular with base portion 582 having inner and outer base surface 582a, 582b, respectively and wall 584, including inner and outer wall surfaces 584a and 584b, respectively. Wall 584 terminates in flat surface 585, the wall "standing up" from base portion 582. As best shown in FIG. 24, outer surface 584b of wall 584 is curved inwardly. Base 582 is sized and shaped such that outer surface 582b of the base fits within third portion 554 of the hole.

Referring to FIG. 24, cap 580 is positioned within hole 540 such that lower surface 581 extends substantially parallel to bone-contacting surface 532. Base 582, and in particular outer surface 582b of the base, is positioned against the inner surface of hole 540. This positioning of the base against the inner surface of the hole creates an opening between the inner surface of the hole and wall 584 into which a portion of nut 571 can be received.

As shown in FIG. 24, nut 571 is sized and shaped to fit within the opening between the inner surface of the hole and wall 584 of the cap. Nut 571 has a substantially spherical shape that has at least one ramp 575 on the outer surface 573 of the nut, shown in FIG. 25. In the illustrated embodiment, outer surface includes four ramps 575. In a variant of the embodiment, shown in FIG. 26, outer surface 573' of nut 571' may include a series of teeth extending around a circumference of the outer surface. In this example, the teeth form concentric ridges extending around the outer surface.

Nut 571 includes ledge 578 extending radially inwardly around inner surface 576 at upper end 572 of the nut. Ledge 578 is threaded to mate with the threads of screw head 562. Ledge 578 sits on flat surface 585 of wall 584, and the nut is received within the space between wall 584 and the inner surface of the hole. In this position, nut 571 can "float" or move polyaxially with respect to cap 580 and hole 540 in a direction along the wall 584 of the cap, but the nut is limited in rotational movement by the ramps on its outer surface 573.

In use, screw 560 is positioned in hole 540 through nut 571 and cap 580 such that non-threaded transition portion 565 of the screw contacts lip 588 of the cap. Nut 571 is moveable along the spherical surface of second portion 554 of the hole to allow for polyaxial orientations of screw 560 in hole 540. Screw 560 may be rotated, and the threads on screw head 562 engage the threads on nut 571 to lock the screw to the nut. Rotation of screw 560 imparts a rotational force on nut 571. As nut 571 is rotated, ramps 575 on outer surface 573 of the nut pinch against the inner surface of the hole to fix the nut in position.

Alternatively, nut 571 may be fixed to the plate at the desired angle by rotation of a tool (not shown). The screw may then be inserted into the hole and rotated to engage the threads of the nut to lock the screw to the nut and the plate.

In yet another embodiment of the present disclosure, FIGS. 28-31 show bone plating system 620 including bone plate 630 with a plurality of holes 640 and screws 660, each with threaded conical head 662 and threaded shaft 668. Each hole 640 includes insert 670 received within the hole and allowing for polyaxial locking of screw 660.

Figure 30:
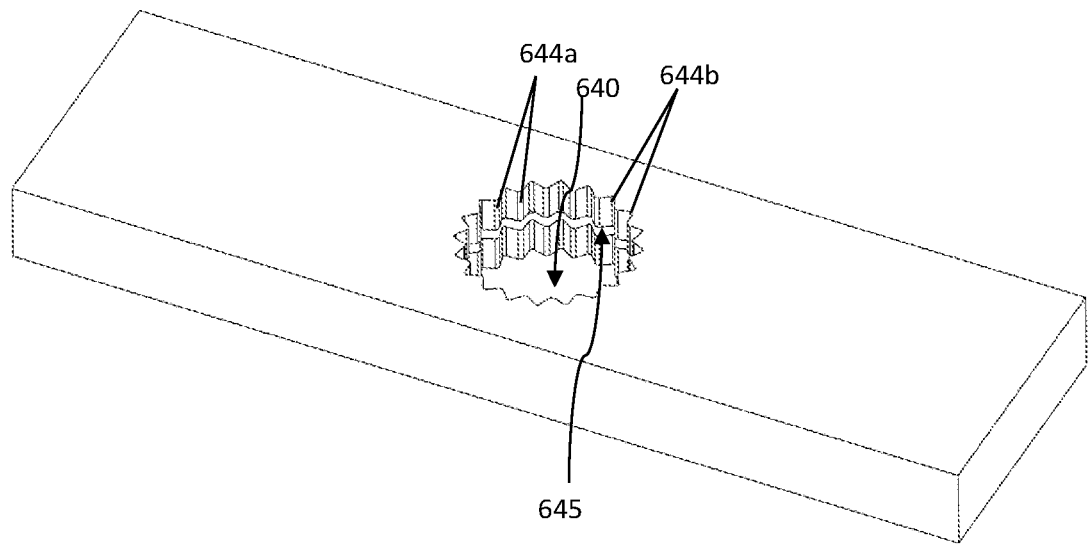
FIG. 30 is a perspective top view of the hole in the plate of the system of FIG. 28.

Referring to FIG. 30, hole 640 includes a plurality of projections 644a extending inwardly toward the center of the hole. In the illustrated embodiment, each projection extends in a direction along a central axis of the hole, and each projection is adjacent a substantially rounded trough 644b. Projections 644a may be separated into two rows and spaced apart from one another along the central axis of the hole by "zig-zag" groove 645. Groove 645 extends around the circumference of the hole.

Figure 31:
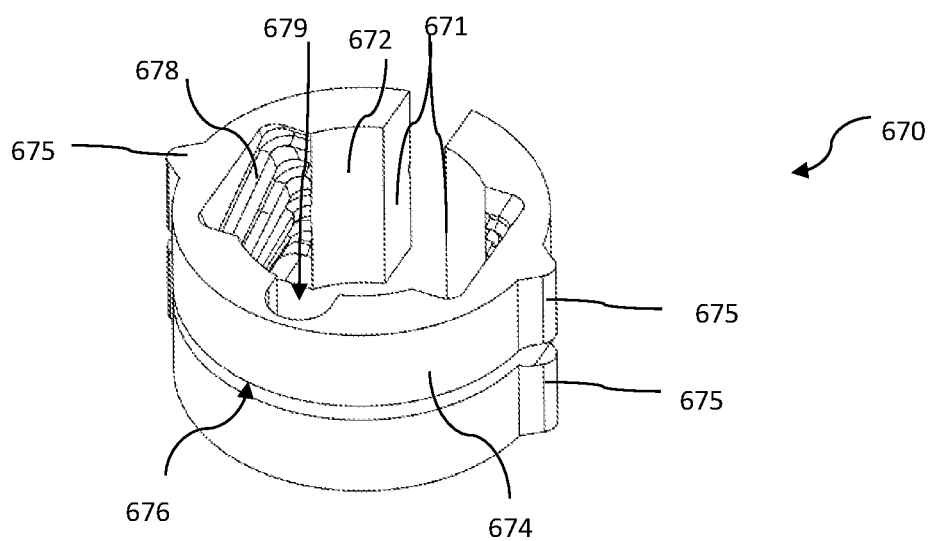
FIG. 31 is a perspective top view of the insert of the system of FIG. 28.

Referring to FIG. 31, insert 670 may be inserted within hole 640 to allow for polyaxial locking of screw 660. Insert 670 has a substantially cylindrical shape and includes inner surface 672 and outer surface 674, opposite the inner surface defining an opening for receiving screw 660. Insert 670 does not form an enclosed annular shape, rather the insert includes two open ends 671 that define an opening between the open ends forming a "C-shape." Two pairs of two rounded tabs 675 project radially outward of outer surface 674 spaced about 180 degrees from one another, the tabs sized and shaped to fit within troughs 644b of hole 640. Recess 676 extends through inner surface 672 and terminates within the body of the insert so as not to extend through outer surface 674. Inner surface 672 includes at least two columns of teeth 678. The columns of teeth 678 have substantially spherical profile, best shown in FIG. 29. Insert 670 further includes curved passage 679 opposite open ends 671 that extends into the body of the insert from inner surface 672 but does not extend through outer surface 674. Although not shown, outer surface 674 of the insert may include serrations to engage the hole.

Insert 670 is rotatable 360 degrees within hole 640 prior to locking of screw 660, which allows for polyaxial orientations of the screw. Insert 670 is secured to the hole by a retaining ring. In use, screw 660 is placed within insert 670, and the screw is moveable along one plane. Screw 660 is rotated, and head 662 forms an interference fit with the columns of teeth of the insert. As the screw is advanced through hole 640, open ends 671 of the insert move away from one another to open the insert. As insert 670 opens tabs 675 engage troughs 644b of the hole to prevent rotational movement of the insert.

Figure 32:
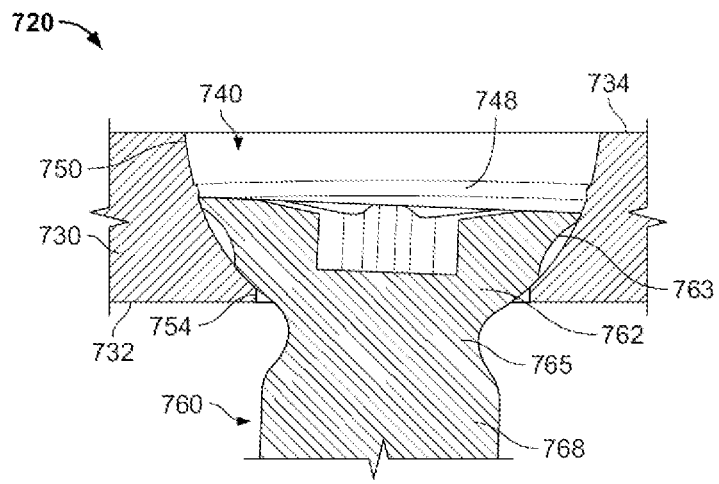
FIG. 32 is a cross-sectional side view of a bone plating system according to another embodiment of the present disclosure.
Figure 33:
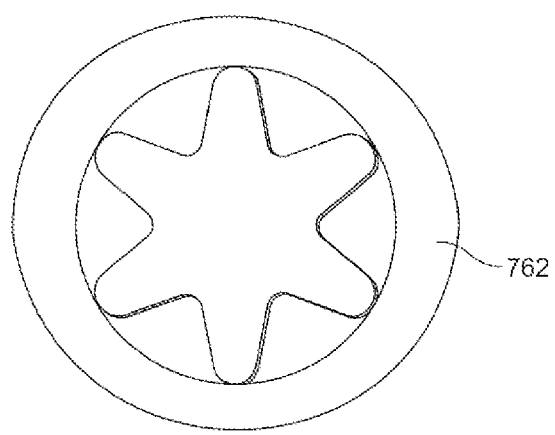
FIG. 33 is a top view of the screw of the system of FIG. 32.

FIGS. 32-33 show bone plating system 720 according to another embodiment of the present disclosure. System 720 includes bone plate 730 having holes 740 and locking screws 760.

Referring to FIG. 32, hole 740 includes first portion 750 extending from upper surface 734 of plate 730 to second portion 754. First portion 750 has a concave shape and includes lip 748 extending around the circumference of the inner surface of hole 740. Second portion 754 extends from first portion 750 to bone-contacting surface 734 of the hole and defines a substantially flat edge. Hole 740 has a larger diameter at upper surface 734 than at bone-contacting surface 732.

Screw 760 includes head 762, shaft 768, and neck 765 extending therebetween. Head 762 includes concave relief portions 763 around the head to allow for easy locking and prevent collision of the head with the hole. From the top view, shown in FIG. 33, head 762 has a substantially oval shape. Neck 765 has a diameter that is smaller than the diameter of the head and of the shaft, as shown in FIG. 32.

In use, the oval shape of head 762 allows the head to snap into lip 748 of hole 740. Head 762 has a roughened outer surface to prevent slipping of the screw head. With the head engaged with lip 748, the lip prevents the screw from pulling out of the hole.

Figure 34:
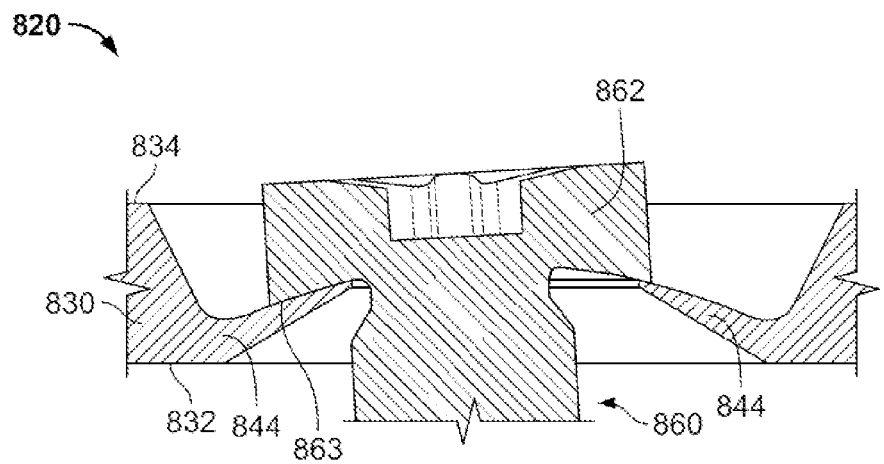
FIG. 34 is a cross-sectional side view of a bone plating system according to another embodiment of the present disclosure.
Figure 35:
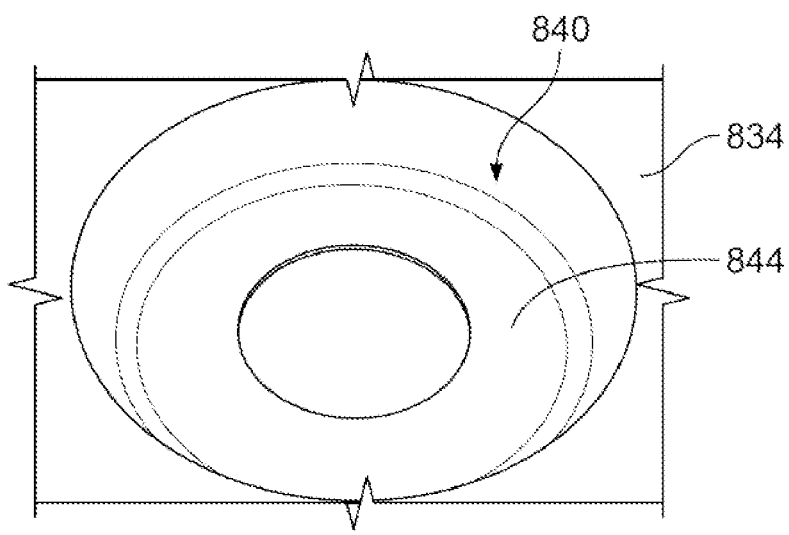
FIG. 35 is a perspective top view of the hole of the plate of the system of FIG. 34.

In yet another embodiment, FIGS. 34-35 show bone plating system 820 of the present disclosure. System 820 includes holes 840 extending through plate 830 from upper surface 834 to bone-contacting surface 832. Holes 840 are configured for polyaxial locking, as will be described below.

Figure 36:
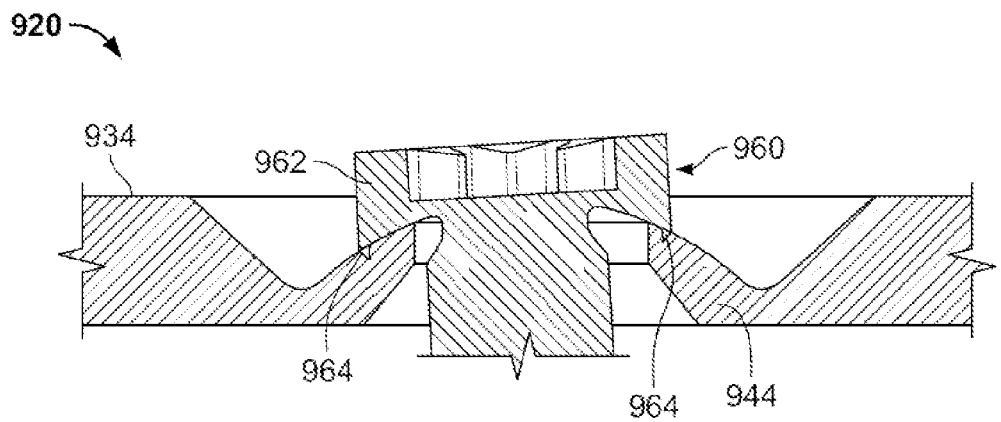
FIG. 36 is a cross-sectional side view of a bone plating system according to another embodiment of the present disclosure.

Hole 840 includes thin engagement section 844 extending inward from an inner surface of the hole toward the center of the hole. Engagement section 844 extends at an angle toward upper surface 834 of the plate as shown in FIG. 36. In the illustrated embodiment, engagement section 844 forms a convex, rounded surface. Engagement section 844 defines an annular opening with a relatively smaller diameter than the diameter of hole 840 at upper surface 834 of the plate.

Screw 860 includes head 862 having a lower surface 863 that rests on engagement section 844 of the hole 840. Lower surface 863 forms a concave surface to mate with the convex surface of the engagement surface. Screw 860 may have a roughened outer surface on head 862 to create surface bonding between the hole and the screw. After screw 860 is inserted in hole 840, the screw is rotated. Rotation of the screw causes engagement section 844 to flex and bend, which creates an opposing force to secure the screw to the plate at variable angles.

Figure 37:
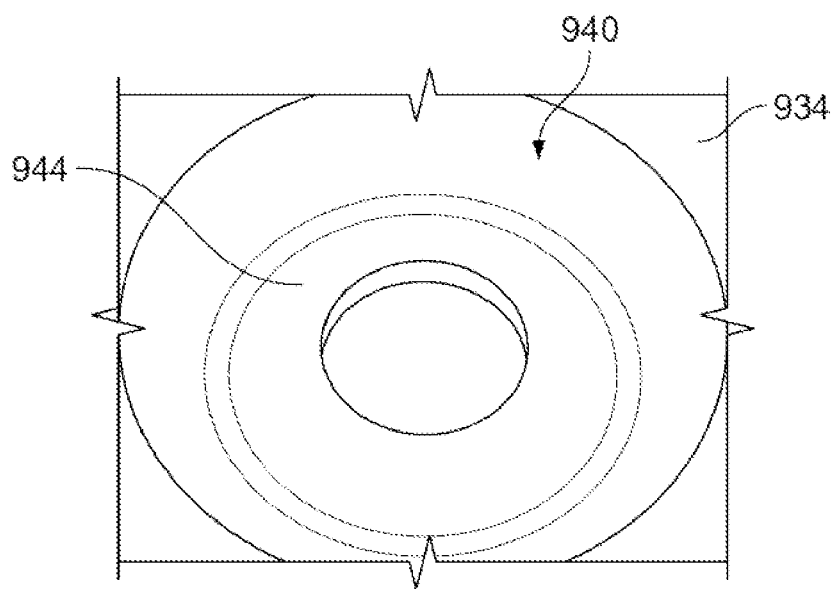
FIG. 37 is a perspective top view of the hole of the plate of the system of FIG. 36.
Figure 38:
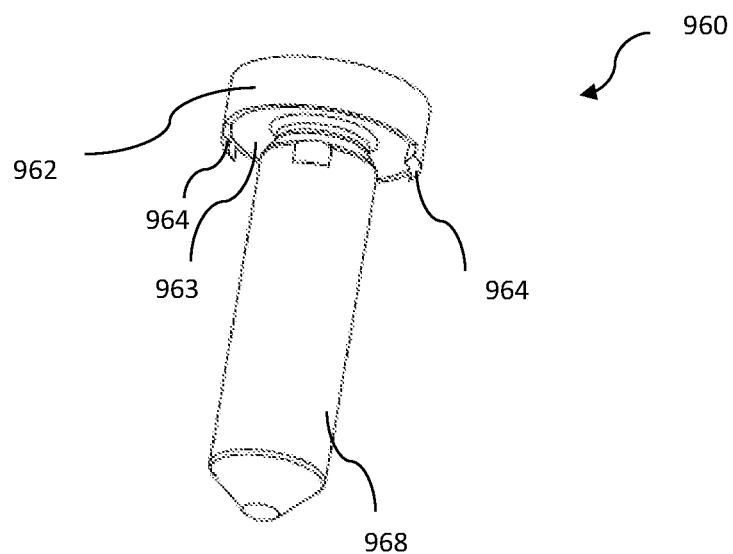
FIG. 38 is a perspective side view of the locking screw of the system of FIG. 36.
Figure 39:
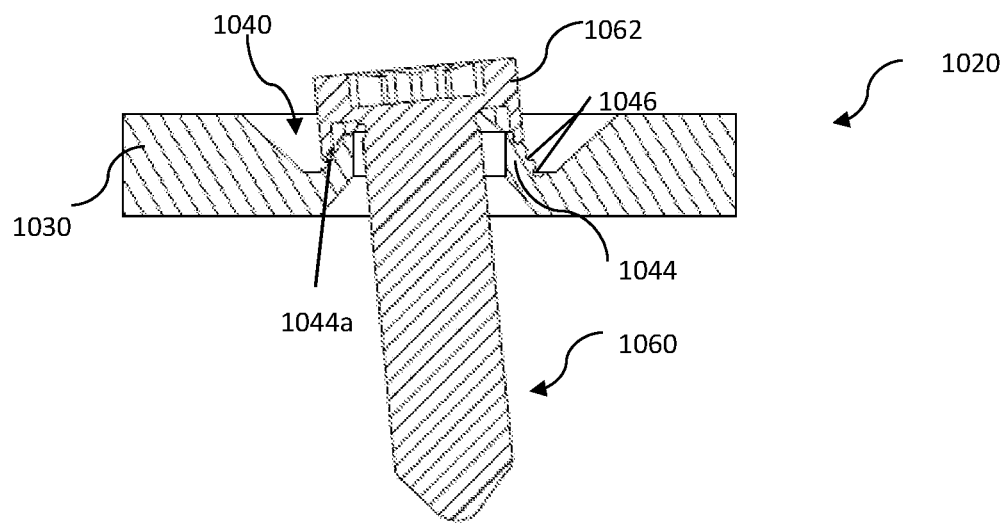
FIG. 39 is a cross-sectional side view of a bone plating system according to another embodiment of the present disclosure.
Figure 40:
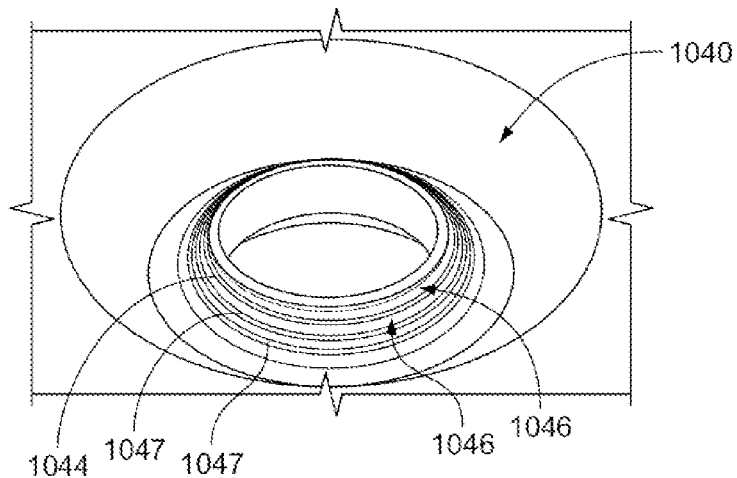
FIG. 40 is a perspective top view of the hole of the plate of the system of FIG. 39.

FIGS. 36-38 show bone plating system 920 according to another embodiment of the present disclosure. System 920 is similar to system 820 and includes plate 930 with holes 940 configured to receive locking screws 960. Holes 940 include engagement section 944, similar in most respects to engagement section 844 of hole 840. Engagement section 944 may be substantially rounded to form a convex surface, as shown in FIGS. 36 and 37.

Screw 960 is similar to screw 860, the similar features of while will not be repeated. Screw head 962 includes at least teeth 964 projecting from lower surface 963 of the screw head in a direction toward a distal end of shaft 968. Teeth 964 may terminate in a sharp point, a knife edge, or may be hooked. In other examples, teeth 964 are shaped in any manner to form a sharp point or edge of the tooth. In the illustrated embodiment, there are two teeth 964 spaced about 180 degrees from each other. Screw 960 is formed of a material that is harder than a material that plate 930 is formed of.

In use, screw 960 is inserted in hole 940, and torqued. As screw 960 is torqued, the sharp edges of teeth 964 of the head 962 dig into engagement section 944 of hole 940 and lock the screw to the hole at the desired angle.

In another embodiment of the present disclosure, FIGS. 39-43 show bone plating system 1020, similar to system 920. System 1020 includes bone plate 1030 with holes 1040 extending through the plate and adapted to receive and lock screw 1060 in polyaxial orientations.

Hole 1040 includes engagement section 1044 similar in most respects to engagement section 944, except that engagement section 1044 includes a plurality of grooves 1046 extending into superior surface 1044a of the engagement section around the circumference of engagement section 1044. Engagement section 1044 further includes a plurality of lips 1047 adapted to engage a corresponding snap feature on screw 1060, further described below. Each lip 1047 is positioned between two grooves 1046.

Figure 41:
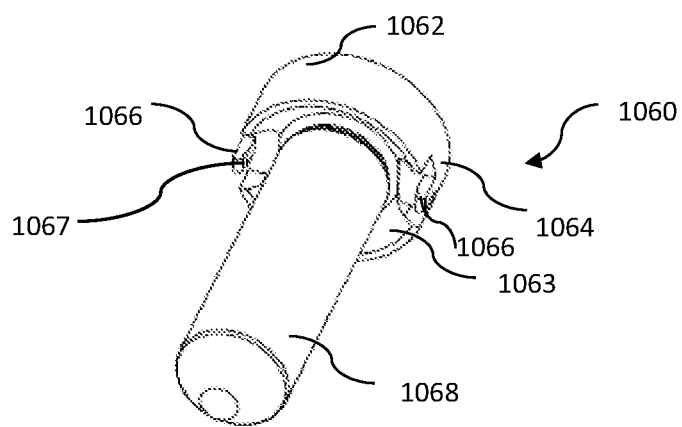
FIG. 41 is a perspective side view of the locking screw of the system of FIG. 39.

Referring to FIG. 41, screw 1060 includes head 1062 have a substantially flat side surface 1063 and a concave lower surface 1063. Lower surface 1064 includes at least one snap feature to grip to grooves 1046 and lips 1047 of the engagement section 1044 of the hole. The illustrated embodiment includes projection 1066 extending along a longitudinal axis from side surface 1063 in a direction toward a distal end of the shaft 1068. Projection 1066 includes at least one groove 1067 extending in a direction transverse to its longitudinal axis. Groove 1067 mates with lips 1047 of the hole to secure the screw 1060 to the hole. In the illustrated embodiment, screw 1060 includes two snap features, namely two projections 1066 spaced 180 degrees apart from one another on head 1062.

In use, screw 1060 is inserted within hole 1040 and torqued. As torque is applied to the screw head 1062, projections 1066 deform to create a snapping effect with lips 1047 and grooves 1047 to lock the projection and the screw to the hole while allowing the screw to be positioned at variable angles.

Figure 42:
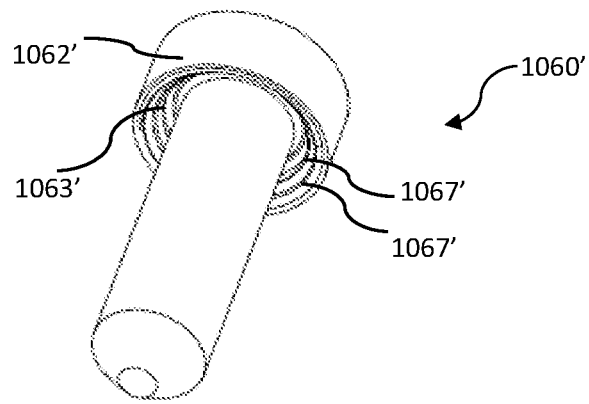
FIG. 42 is a perspective side view of a variation of a locking screw of the system of FIG. 39.
Figure 43:
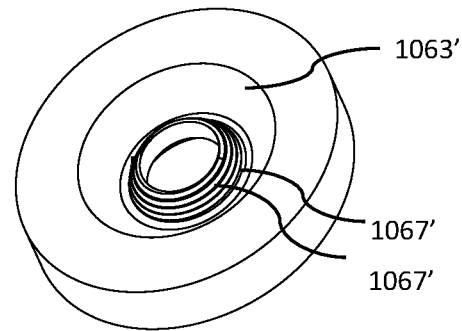
FIG. 43 is a perspective bottom view of the screw head of the locking screw of FIG. 42.
Figure 44:
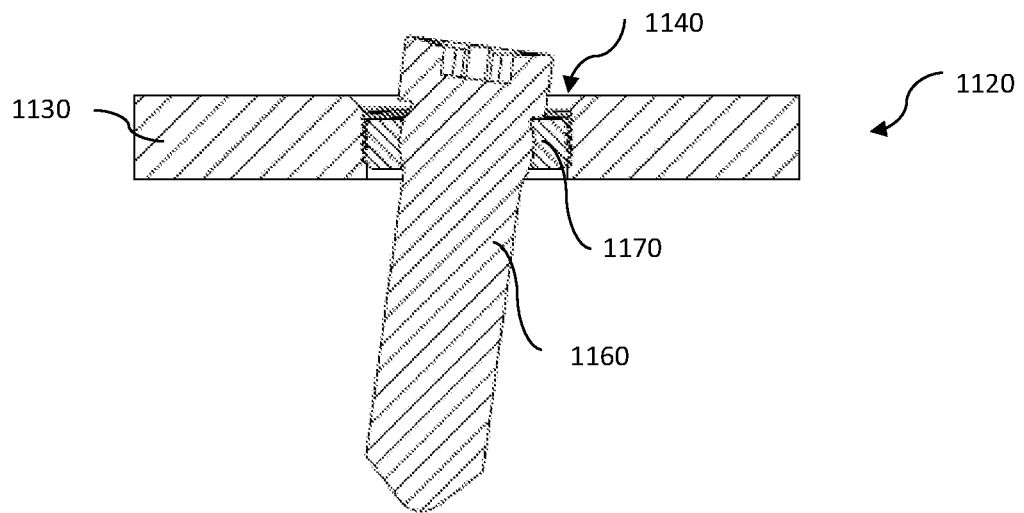
FIG. 44 is a cross-sectional view of a bone plating system according to another embodiment of the present disclosure.
Figure 45:
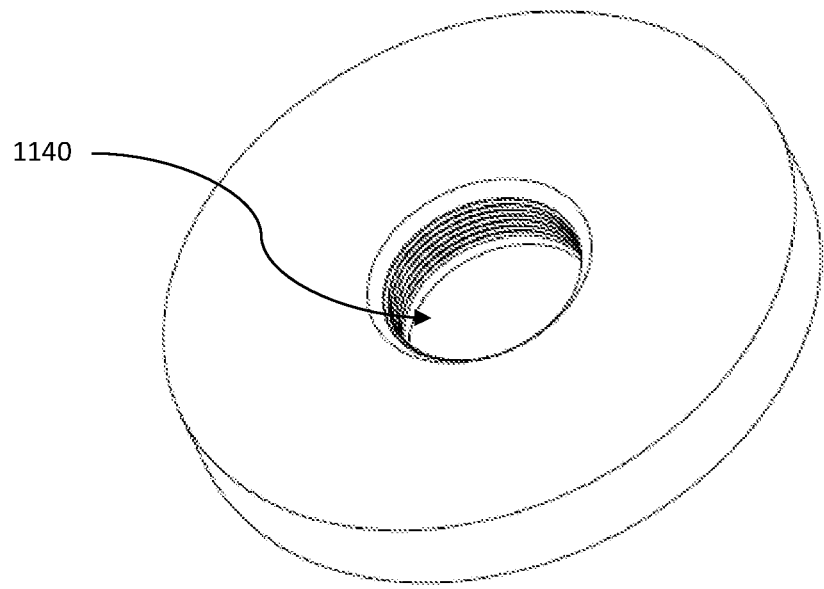
FIG. 45 is a perspective top view of the hole of the plate of the system of FIG. 44.
Figure 46:
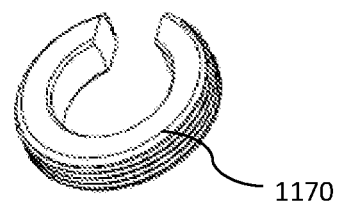
FIG. 46 is a perspective side view of the washer of the system of FIG. 46.

FIGS. 42-43 show a variant of bone system 1020 having screw 1060' that differs from screw 1060. Screw 1060' includes a plurality of grooves 1067' on concave lower surface 1063' of the head 1062'. Grooves 1067' extend around the lower surface and may be helically wound around the head; alternatively, the grooves extend in parallel, concentric planes around the lower surface of the head. Grooves 1067' mate with the lips of the engagement section of the hole and snap onto the lips to lock the screw head to the hole in polyaxial orientations. In both variants of system 1020, grooves 1067 of the engagement section of the hole provide higher bending stiffness to the engagement stiffness.

Figure 47:
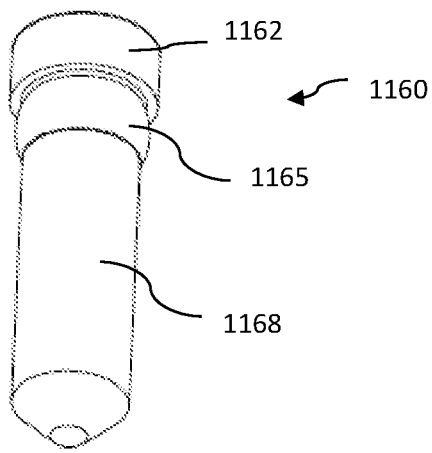
FIG. 47 is a perspective side view of the locking screw of the system of FIG. 44.
Figure 48:
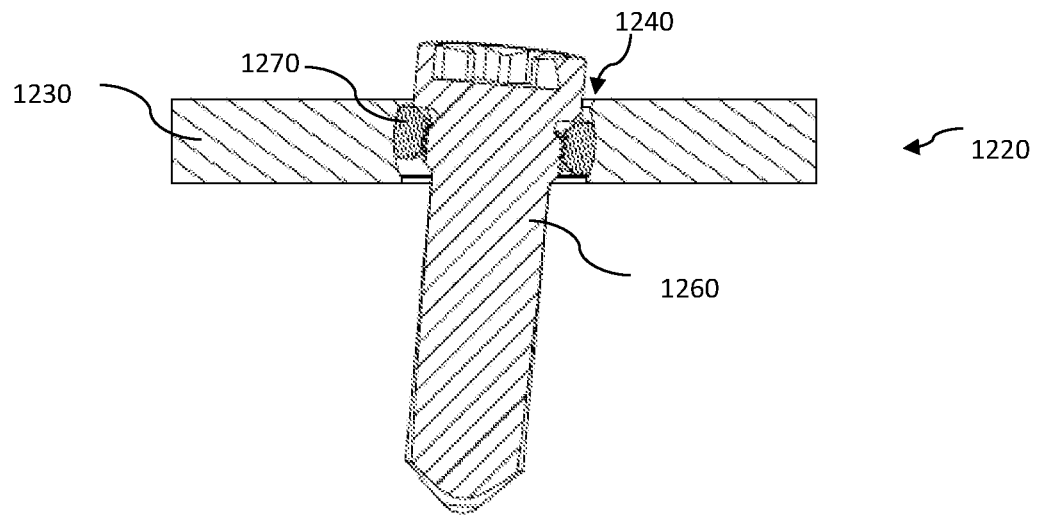
FIG. 48 is a cross-sectional side view of a bone plating system according to another embodiment of the present disclosure.
Figure 49:
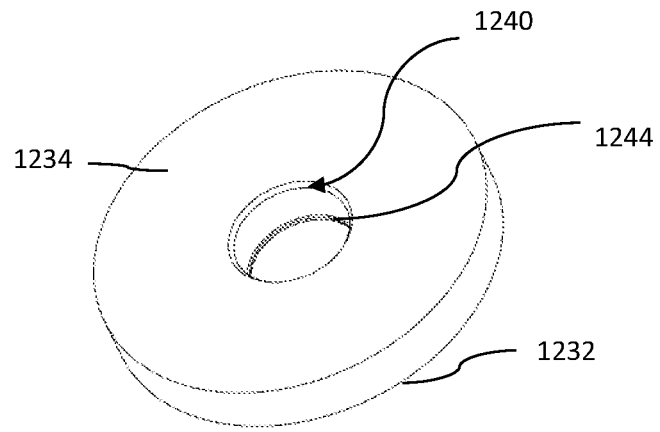
FIG. 49 is a perspective top view of the hole of the plate of the system of FIG. 48.

In yet another embodiment of the present disclosure, FIGS. 44-47 show bone plating system 1120 having holes 1140 for receiving screws 1160 in polyaxial orientations. Holes 1140 are threaded to mate with the threading on screw head 1162. System 1120 includes washer 1170 which is "C-shaped" and includes external threads for locking the washer to the hole. Further, washer 1170 has a substantially concave inner surface. As shown in FIG. 47, screw 1160 includes head 1162, shaft 1168, and transition portion 1165 therebetween. Transition portion 1165 has a convex shape.

In use, washer 1170 is positioned around transition portion 1165 and inserted into hole 1140. The external threads on washer 1170 mate with the threads of hole 1140 to secure the washer to the plate. Due to the convex shape of transition portion 1165 of screw 1160 and the concave shape of the inner surface of washer 1170, the screw-washer interface acts as a ball-and-socket joint, and the screw can move polyaxially. The screw may have a rough surface finish to secure the screw to the washer.

Figure 50:
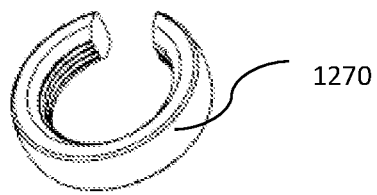
FIG. 50 is a perspective side view of the washer of the system of FIG. 48.
Figure 51:
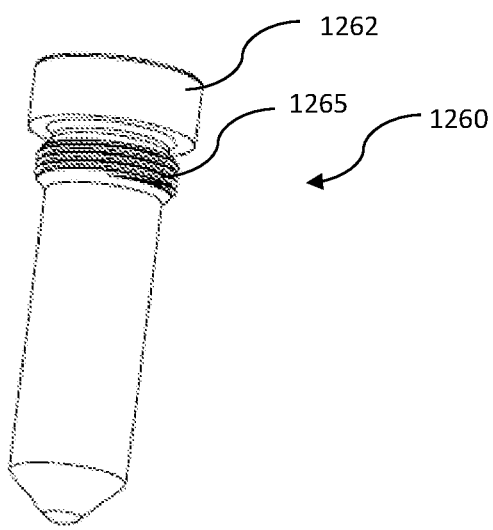
FIG. 51 is a perspective side view of the locking screw of the system of FIG. 48.

FIGS. 48-51 show bone plating system 1220 that is similar in most respects to bone plating system 1120, the similar features of which will not be described again. System 1220 includes plate 1230 with a plurality of holes 1240. Each hole 1240 has a substantially concave shape and includes a single lip 1244 positioned closer to bone-contacting surface 1232 than upper surface 1234. Hole 1240 includes "C-shaped" washer 1270 assembled to the hole and secured therein by snap fit. Washer 1270 includes internal threads, as shown in FIG. 50. Screw 1260 includes head 1262, shaft 1268, and transition portion 1265 therebetween. Transition portion 1265 is convex, and includes external threads to mate with the threads of washer 1270.

In use, the threads of transition portion 1265 of screw 1260 engage the threads of washer 1270 to rigidly lock the screw to the washer. The convex surface of the transition portion 1265 and the concave surface of the washer form a ball-and-socket joint to allow for polyaxial locking of the screw. Lip 1244 on plate hole 1240 restricts movement of the washer beyond the lip.

Figure 52:
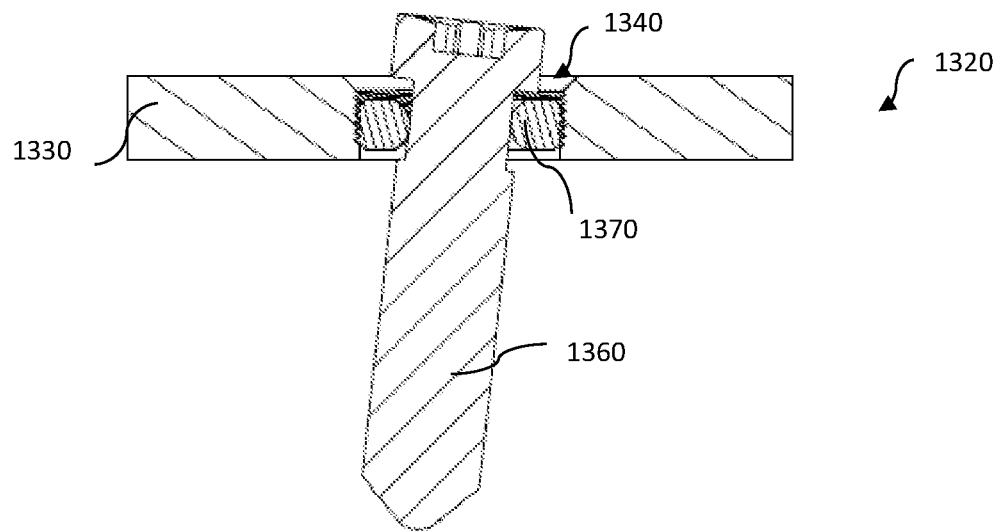
FIG. 52 is a cross-sectional side view of a bone plating system according to another embodiment of the present disclosure.

FIG. 52 shows bone plating system 1320 of the present disclosure which is identical in most respects to bone plating system 1120, described above. Each hole 1340 of plate 1330 includes washer 1370 that has a rounded inner surface to engage screw 1360.

Figure 53:
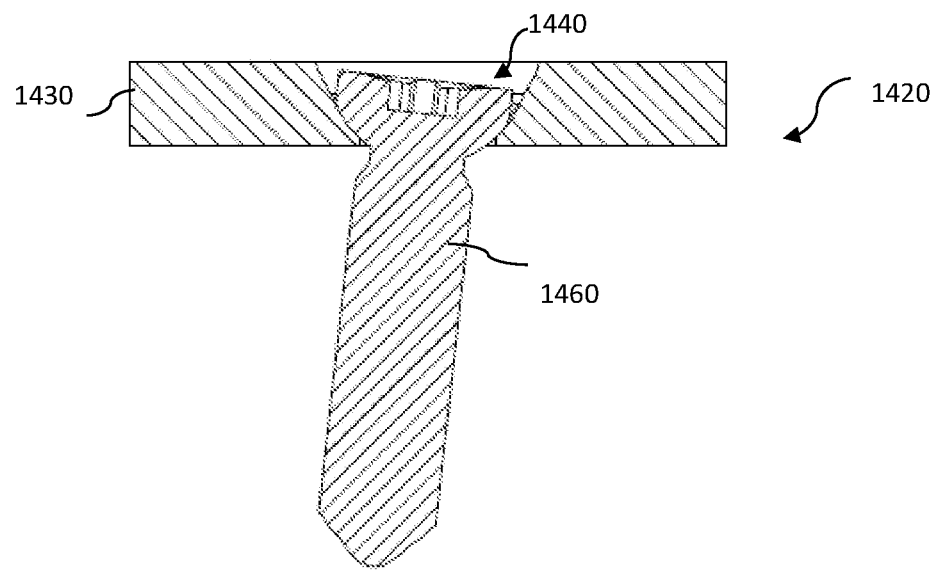
FIG. 53 is a cross-sectional side view of a bone plating system according to another embodiment of the present disclosure.
Figures 54A, 54B:
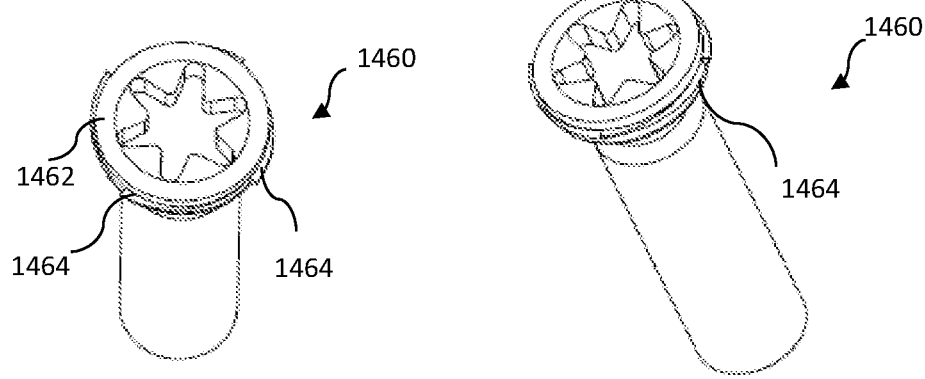
FIGS. 54A and 54B are perspective top and side views of the locking screw of the system of FIG. 53.

In yet another embodiment, FIGS. 53-54 show bone plating system 1420 of the present disclosure. System 1420 includes plate 1430 having holes 1440 extending through the plate for receiving screws 1460 in polyaxial orientations.

Screws 1460 include at least one sharp cutting edges 1464 on head 1462 to shear into plate 1430. In the illustrated embodiment, shown in FIGS. 54A and 54B, the cutting edges 1464 extend around the circumference of the screw head. The screw is designed to fix in variable angles with respect to a central axis of the hole due to the deformation of the plate from the cutting edges 1464 of the screw head. The screw is formed of a material harder than the plate to enable the tapping of the plate and securing of the screw.

Figure 55:
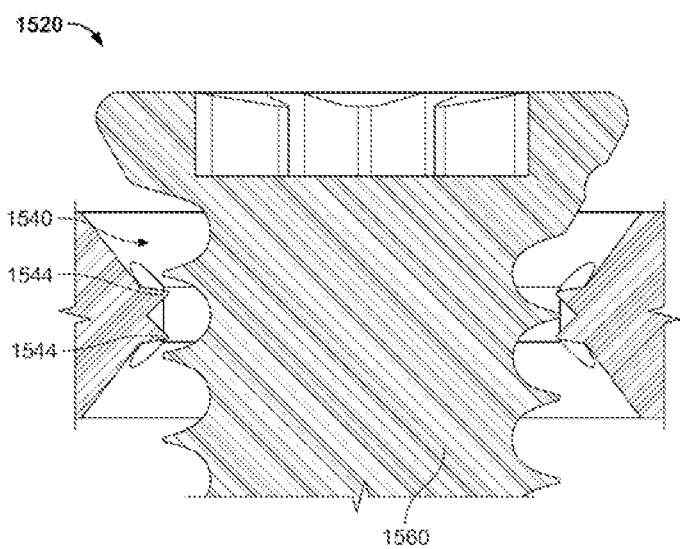
FIG. 55 is a cross-sectional side view of a bone plating system according to another embodiment of the present disclosure.
Figure 56:
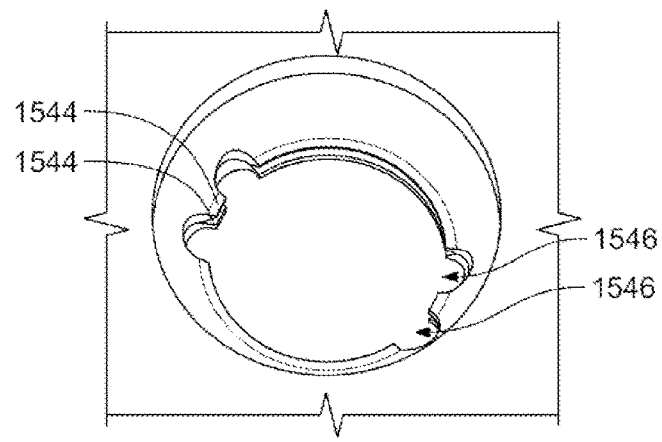
FIG. 56 is a perspective top view of the hole of the plate of the system of FIG. 55.

In yet another embodiment of the present disclosure, FIGS. 55-56 show bone plating system 1520 including plate 1530 having holes 1540 for accommodating screw 1560 in variable angles. As shown in FIG. 56, each hole 1540 includes two lips 1544 extending around the circumference of the hole and acting as threads to mate with screw 1560. Each lip 1544 is interrupted in its path around the hole by a plurality of rounded recesses 1546 extending into the inner surface of the hole. As shown in FIG. 55, the lips have a "V-shape" cross-section. Screw 1560 is threaded and includes opposing convex and concave surfaces. The V-shape of the lips accommodates both the concave and convex surfaces of the screw. As torque is applied to screw 1560, the threads of the screw lock to lips 1544 to secure the screw to the plate.

Figure 57:
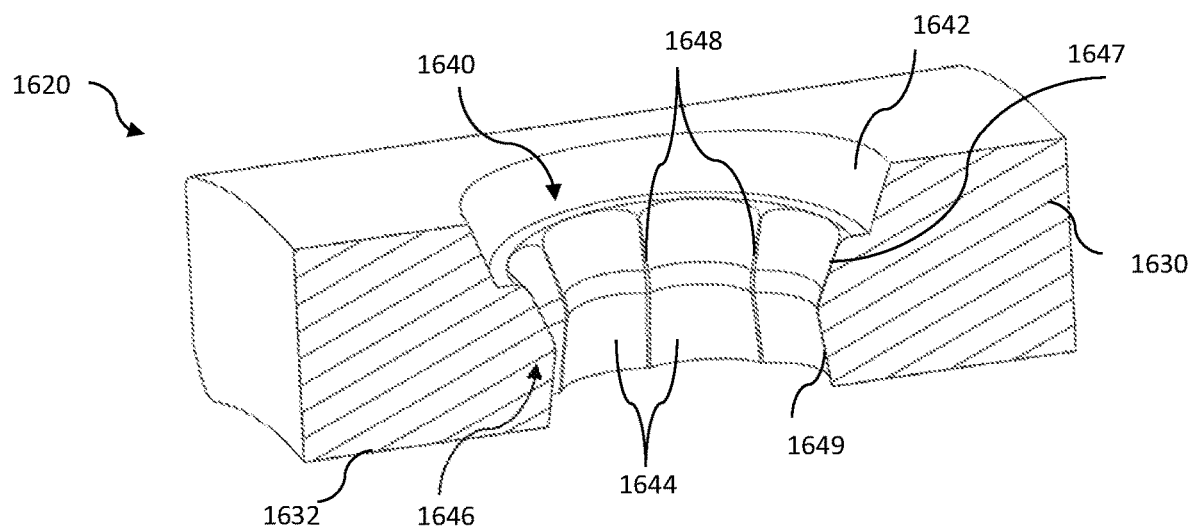
FIG. 57 shows a cross-sectional view of a hole according to another embodiment of the present disclosure.
Figure 58:
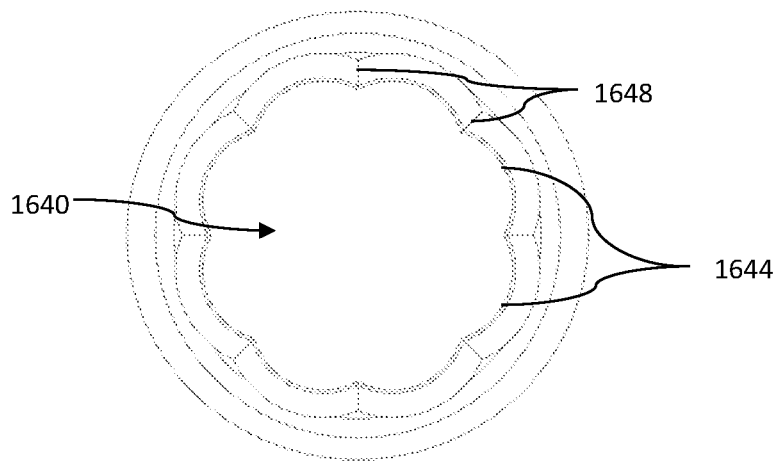
FIG. 58 is a top view of the hole of FIG. 57.
Figure 59:
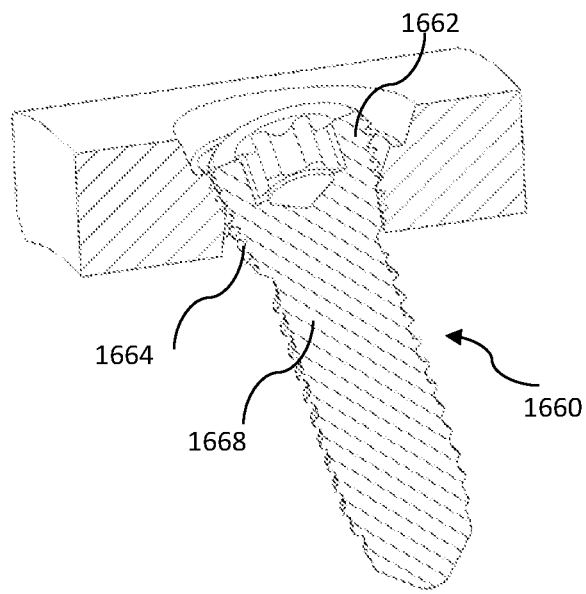
FIG. 59 is a cross-sectional view of the hole of FIG. 57 in conjunction with a locking bone screw.

FIGS. 57-59 show bone plating system 1620 which includes plate 1630 with holes 1640 for receiving locking screws 1660 at polyaxial orientations. As shown in FIG. 57, each hole 1640 includes countersink 1642 and engagement region 1646 extending from the countersink to bone-contacting surface 1632.

As shown in FIG. 58, from the top view, hole 1640 has a flower-shape configuration formed from a plurality of spaced apart scalloped regions 1644 and screw-engaging members 1648 which are spaced apart about the central axis of hole 1640. Each screw-engaging member 1648 extends in a direction from countersink 1642 toward bone-contacting surface 1632 and separates adjacent scalloped regions 1644. In the illustrated embodiment, hole 1640 includes eight equally spaced apart screw-engaging members 1648 and scalloped regions 1644. In this embodiment, each screw-engaging member 1648 defines a surface defining a width as it extends in a direction parallel to the central axis of the hole. As shown in FIG. 57, engagement region 1646 has a converging-diverging profile, in which an upper portion 1647 tapers toward the central axis of hole 1640 and a lower portion 1649 tapers away from the central axis of the hole 1640. Although shown with a specific number of scalloped regions and engaging members, it is to be understood that different embodiments according to the present invention may exhibit any number of each element.

FIG. 59 shows locking screw 1660 positioned within hole 1640. Locking screw 1660 includes a conically shaped head 1662 having threads 1664 and a threaded shaft 1668. When locking screw 1660 is positioned within hole 1640, threads 1664 engage screw-engaging members 1648 of hole 1640 by plastically deforming the screw-engaging members 1648 to secure the locking screw 1660 to the bone plate 1630 at variable angles. Other screw designs can also be utilized, for instance, screws with curved or rounded heads.

Figure 60:
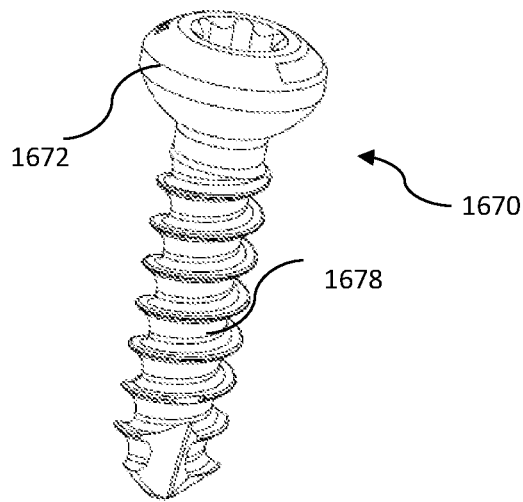
FIG. 60 is a side perspective view of a non-locking screw for use with the hole of FIG. 57.

Holes 1640 are configured to receive non-locking screws 1670 in addition to locking screws 1660. As shown in FIG. 60 non-locking screw 1670 has a substantially rounded head 1672 and a threaded shaft 1678. This type of screw may or may not interact with any of the elements of the screw hole in which they are placed.

Figure 61:
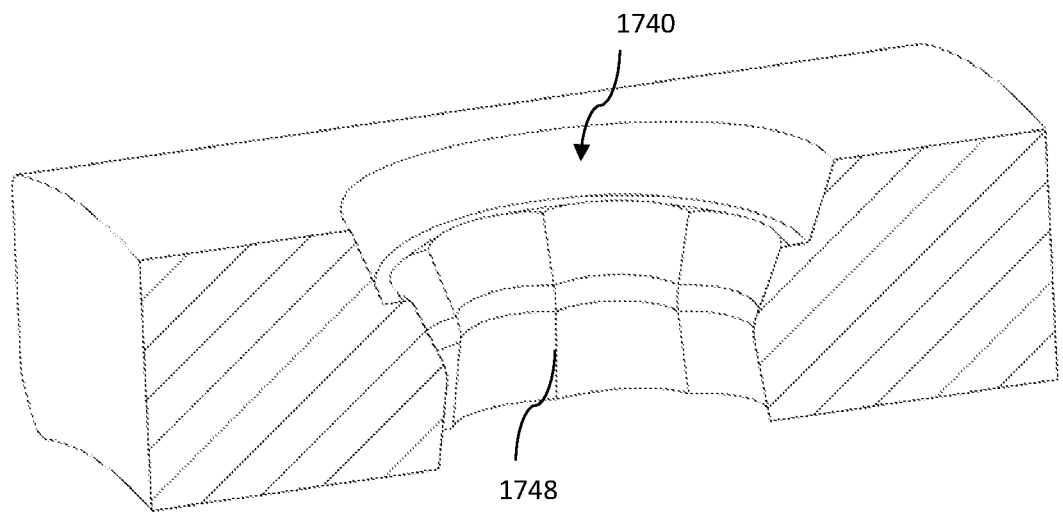
FIG. 61 is a cross-sectional view of an alternative embodiment of the hole of FIG. 57.

FIG. 61 shows hole 1740 which is identical to hole 1640 except that each screw-engaging members 1748 defines a line rather than a surface as in hole 1640.

Figure 62:
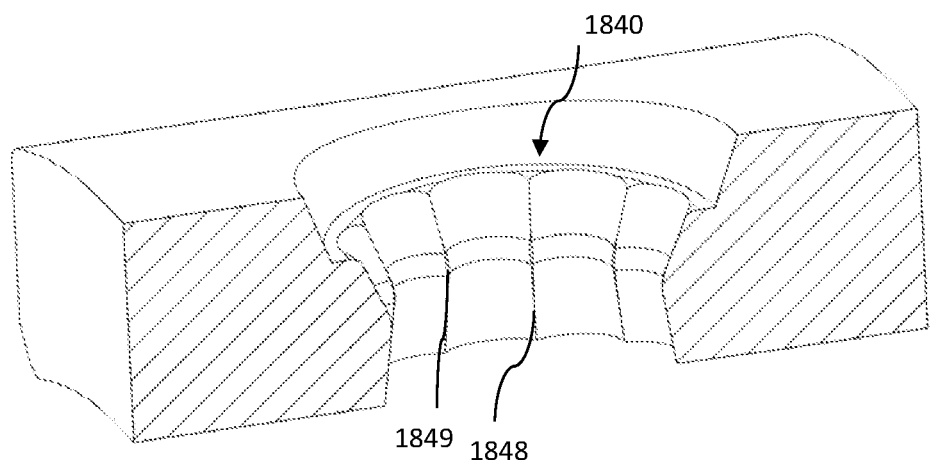
FIG. 62 is another alternative embodiment of the hole of FIG. 57.
Figure 63:
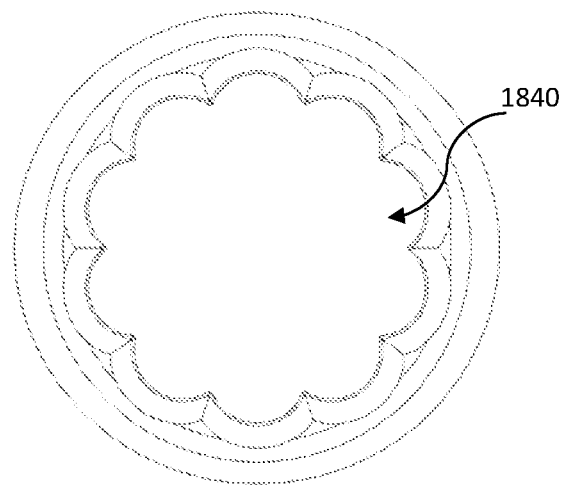
FIG. 63 is a top view of the hole of FIG. 62.

FIGS. 62 and 63 show hole 1840 which is an alternative embodiment of holes 1640 and 1740. Each screw-engaging member 1848 includes a line that transitions into a diamond-shaped surface 1849. Locking screw 1660 engages and plastically deforms the diamond-shaped surface 1849 to secure the screw to the hole. Further, hole 1840 differs from hole 1640 in that it includes ten equally spaced apart screw-engaging members 1848, as shown in FIG. 63.

Figure 64:
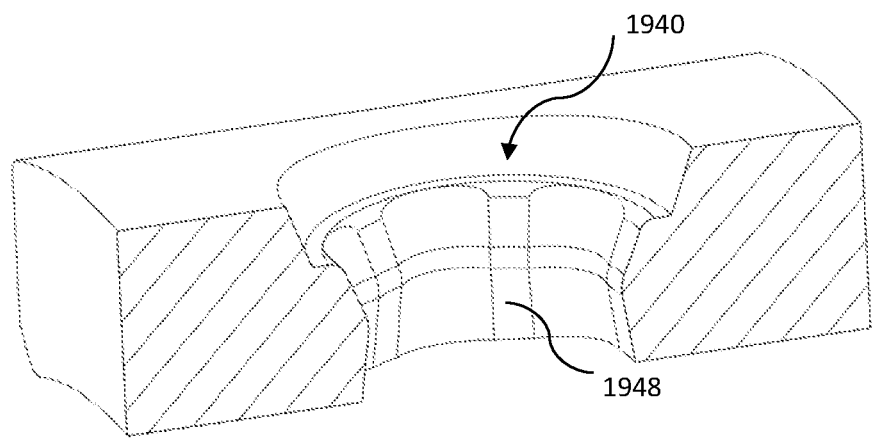
FIG. 64 is a cross-sectional view of yet another alternative embodiment of the hole of FIG. 57.
Figure 65:
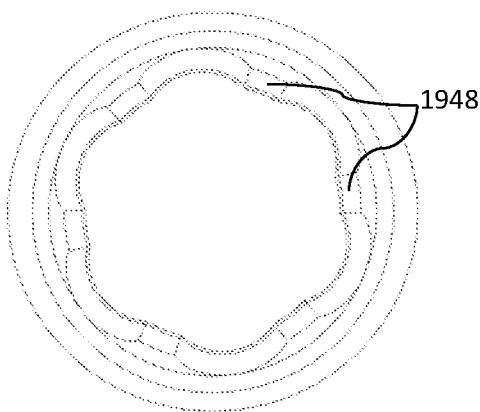
FIG. 65 is a top view of the hole of FIG. 64.

FIGS. 64 and 65 show hole 1940 which is similar to hole 1640 except that screw-engaging members 1948 of hole 1940 form a wider surface with a substantially constant width along the length of the surface of each member 1948.

During insertion of a locking screw in any of holes 1640, 1740, 1840, and 1940, a locking screw, such as locking screw 1660, is torqued within the hole. As the screw head rotates, the threads 1664 of screw head 1662 engage at least some of the screw-engaging members 1648 to form an interference connection between the screw-engaging members and the screw head which causes the screw-engaging members to plastically deform. This connection results in the locking of the screw to the plate and prevents subsequent loosening of the screw.

The plates described above are formed from a single piece of rigid material, such as stainless steel, titanium and its alloys. In other examples, the plates may be formed from other biocompatible materials including bioceramics and polymers. In some instances, the locking screws may be formed of cobalt chromium and may be harder than the material of the plate. In other instances the screws may be formed of stainless steel, titanium and its alloys, etc. It is contemplated to form the plates utilizing any known manufacturing method, including molding, milling and additive manufacturing.

It will be appreciated that the features described in connection with individual embodiments may be shared with others of the described embodiments. Further, individual plates may include one or more the described hole designs.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone plate comprising:
    a bone-contacting surface;
    an upper surface opposite the bone-contacting surface; and
    a hole extending from the upper surface to the bone-contacting surface, the hole having a plurality of scalloped regions spaced around a circumference of the hole being separated by a respective screw-engaging member that is plastically deformable to form an interference connection with a screw head, the screw-engaging member having a converging-diverging profile that extends along a central axis of the hole, the hole further defining a countersink that extends from the upper surface to an intermediate surface, wherein the intermediate surface extends into the hole along a plane that is perpendicular to the central axis, and the screw-engaging member extends between the intermediate surface and the bone-contacting surface.

2. The bone plate of claim 1, wherein the screw-engaging member includes a surface.

3. The bone plate of claim 2, wherein the surface defines a rectangle or diamond shaped.

4. The bone plate of claim 2, further comprising a first line and a second line extending in a direction of the central axis of the hole, the surface being positioned between each of the first and the second line.

5. The bone plate of claim 1, wherein the screw-engaging member includes a line.

6. The bone plate of claim 1, wherein the hole is configured to secure both of a locking screw and a non-locking screw within the plate.

7. The bone plate of claim 1, wherein the hole includes at least eight scalloped regions.

8. A system for peri-prosthetic repair comprising:
    the bone plate of claim 1; and
    a locking screw configured to be secured within the hole of the plate, wherein a head of the locking screw has a first hardness and the screw-engaging member has a second hardness that is softer than the first hardness.

9. The system of claim 8, further comprising a non-locking screw configured to be received within the hole.

10. The bone plate of claim 1, wherein the screw-engaging member includes an upper region, a middle region, and a lower region that extend circumferentially around the hole.

11. The bone plate of claim 10, wherein the middle region is positioned closer to the central axis of the hole than the upper and lower regions.

12. A bone plate system comprising:
    a plate including a hole extending from an upper surface to a bone-contacting surface, the hole having a plurality of scalloped regions spaced around a circumference of the hole separated by a respective screw-engaging member that is plastically deformable, the screw-engaging member having a converging-diverging profile that extends along a central axis of the hole, the hole further defining a countersink that extends from the upper surface to an intermediate surface, wherein the intermediate surface extends into the hole along a plane that is perpendicular to the central axis, and the screw-engaging member extends between the intermediate surface and the bone-contacting surface; and
    a screw having a screw head to form an interference connection with the screw-engaging member.

13. The system of claim 12, further comprising a non-locking screw configured to be received within the hole.

14. The system of claim 12, wherein the screw head has a first hardness and the screw-engaging member has a second hardness that is softer than the first hardness.

15. The system of claim 12, wherein the screw-engaging member includes a surface.

16. The system of claim 15, wherein the surface is rectangular shaped or diamond shaped.

17. The system of claim 15, further comprising a first line and a second line extending in a direction of the central axis of the hole, the surface being positioned between each of the first and the second line.

18. The system of claim 12, wherein the screw-engaging member includes a line.

19. A bone plate system comprising:
a plate including a hole extending from an upper surface to a bone-contacting surface, the hole having a plurality of scalloped regions spaced around a circumference of the hole separated by a respective screw-engaging member that has a surface and a converging-diverging profile that extends along a central axis of the hole, the hole further defining a countersink that extends from the upper surface to an intermediate surface, wherein the intermediate surface extends into the hole along a plane that is perpendicular to the central axis of the hole, and the screw-engaging member extends between the intermediate surface and the bone-contacting surface;
a screw having a screw head to form an interference connection with the screw-engaging member;
wherein the screw head has a first hardness and the screw-engaging member has a second hardness that is softer than the first hardness.

* * * * *